US012559472B2

(12) United States Patent
Li et al.

(10) Patent No.: US 12,559,472 B2
(45) Date of Patent: Feb. 24, 2026

(54) SALTS OF A COMPOUND AND THE CRYSTALLINE FORMS THEREOF

(71) Applicant: HUTCHISON MEDIPHARMA LIMITED, Shanghai (CN)

(72) Inventors: Wenji Li, Shanghai (CN); Ling Feng, Shanghai (CN)

(73) Assignee: HUTCHISON MEDIPHARMA LIMITED, Shanghai (CN)

( * ) Notice: Subject to any disclaimer, the term of this patent is extended or adjusted under 35 U.S.C. 154(b) by 835 days.

(21) Appl. No.: 17/768,951

(22) PCT Filed: Oct. 13, 2020

(86) PCT No.: PCT/CN2020/120594
§ 371 (c)(1), (2) Date: Apr. 14, 2022

(87) PCT Pub. No.: WO2021/073494
PCT Pub. Date: Apr. 22, 2021

(65) Prior Publication Data

US 2023/0121346 A1 Apr. 20, 2023

(30) Foreign Application Priority Data

Oct. 14, 2019 (CN) ......................... 201910973785.3

(51) Int. Cl.
*C07D 401/12* (2006.01)

(52) U.S. Cl.
CPC ........ *C07D 401/12* (2013.01); *C07B 2200/13* (2013.01)

(58) Field of Classification Search
CPC .................................................... C07D 401/12
See application file for complete search history.

(56) References Cited

U.S. PATENT DOCUMENTS 9,701,680 B2 * 7/2017 Su ........................ C07D 405/14

FOREIGN PATENT DOCUMENTS

| | | | | |
|---|---|---|---|---|
| WO | WO 2014/139465 A1 | 9/2014 | | |
| WO | WO-2014139145 A1 * | 9/2014 | ................ | A61P 5/00 |
| WO | WO 2018/099451 A1 | 6/2018 | | |

OTHER PUBLICATIONS

Bernstein, J., "Polymorphism in Molecular Crystals", *Oxford University Press*, (2002).

Berge, S. et al., "Pharmaceutical Salts," J. Pharm. Sci., vol. 66, No. 1, pp. 1-19, (1977).

English machine translation of Tsutsumi, S., "A Practice of Physicochemical Study of Drug Substance and Formulation Development Collaborated with Drug Discovery Research," Journal of Pharmaceutical Science and Technology, vol. 72, No. 3, 5 pages, (2012), downloaded on Apr. 24, 2025.

Hilfiker, R. et al., Polymorphism in the Pharmaceutical Industry, 19 pages, (2006).

Tsutsumi, S., "A Practice of Physicochemical Study of Drug Substance and Formulation Development Collaborated with Drug Discovery Research," Journal of Pharmaceutical Science and Technology, vol. 72, No. 3, 5 pages, (2012), Japanese language.

* cited by examiner

*Primary Examiner* — John S Kenyon
*Assistant Examiner* — Rehana Ismail
(74) *Attorney, Agent, or Firm* — Hoxie & Associates LLC

(57) ABSTRACT

The present invention relates to the salts of a compound and the crystalline forms thereof. More specifically, the present invention belongs to the pharmaceutical field, and provides the pharmaceutically acceptable salts of the compound.

16 Claims, 12 Drawing Sheets

SALTS OF A COMPOUND AND THE CRYSTALLINE FORMS THEREOF

CROSS REFERENCE TO RELATED APPLICATIONS

This application is a United States Application under 35 U.S.C. § 371 claiming priority to, and the benefit of, International Application No. PCT/CN2020/120594, filed on Oct. 13, 2020, which claims priority to Chinese patent application No. 201910973785.3, filed on Oct. 14, 2019, which is incorporated by reference in its entirety herein for all purposes.

FIELD OF THE INVENTION

The present invention belongs to the pharmaceutical field, and provides the pharmaceutically acceptable salts of the compound 4-chloro-3-(2-(2-((4-((3S,5R)-3,5-dimethylpiperazin-1-yl) phenyl)amino)pyrimidin-5-yl)ethyl)-5-methoxy-N-methylbenzamide and the crystalline forms thereof, the pharmaceutical compositions comprising the same as well as the methods of preparing the same and the use thereof.

BACKGROUND OF THE INVENTION

Fibroblast growth factor (FGF) has been recognized as an important mediator in many physiological processes. The fibroblast growth factor receptor family of receptor tyrosine kinases consists of four members (FGFR1, FGFR2, FGFR3, and FGFR4). Fibroblast growth factors (FGF) and their receptors (FGFR) play important roles in cell proliferation, cell differentiation, cell migration, cell survival, protein synthesis, and angiogenesis. There are many evidences directly linking FGF signaling to cancer. Dysregulation of FGFR signaling has been implicated in a number of cancers, including squamous non-small cell lung cancer (squamous NSCLC), small cell lung cancer (SCLC), gastric cancer, liver cancer, breast cancer, ovarian cancer, endometrial cancer, and bladder cancer. For example, FGFR1 amplification has been found in 22% squamous NSCLC, FGFR2 amplification has been reported in up to 10% gastric cancer, and FGFR3 mutation has been found in approximately 50-60% non-muscle invasive bladder cancer and 17% of high-grade bladder cancer. Therefore, inhibition of FGFR activity is useful for treating proliferation diseases, such as cancer.

PCT patent application WO2014/139465A1 disclosed the compound 4-chloro-3-(2-(2-((4-((3S,5R)-3,5-dimethylpiperazin-1-yl)phenyl)amino)pyrimidin-5-yl)ethyl)-5-methoxy-N-methylbenzamide for the first time (i.e. Compound 78 in WO2014/139465A1) as well as the preparation thereof. The structure of the compound is shown as follows:

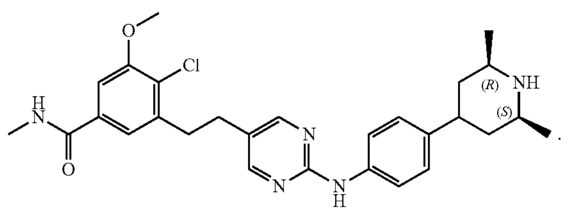

Studies have shown that the compound 4-chloro-3-(2-(2-((4-((3S,5R)-3,5-dimethylpiperazin-1-yl)phenyl)amino)pyrimidin-5-yl)ethyl)-5-methoxy-N-methylbenzamide can effectively inhibit FGFR activity. Thus, it is useful for preventing and treating diseases responsive to inhibition of FGFR activity, such as cancer.

Many compounds may exist in several crystalline forms or in amorphous form. However, for a given compound, it is highly unpredictable (1) whether the compound will exhibit polymorphism, (2) how to prepare such unknown crystalline forms, and (3) how the properties of such unknown crystalline forms are, for example, stability, solubility, flowability, pharmacokinetic parameters, and in vivo bioavailability may vary depending on crystalline forms. See J. Bernstein "Polymorphism in Molecular Crystals", Oxford University Press, (2002).

Forming a salt of a compound will not change the biological activity of the compound itself, but can change the physicochemical properties of the compound. For a given compound, it is highly unpredictable which salts of the compound have better physicochemical properties than the free compound. It is even more impossible to further predict which salts can form crystalline forms with favorable properties, in view of the unpredictability of crystal formation and crystal properties.

Since the properties of a solid material depend on the compound per se and the microstructure of the solid, different solid forms of a compound often show different physicochemical properties as well as different biopharmaceutical properties. Differences in physicochemical properties and biopharmaceutical properties can be determined through a variety of technical means, and can ultimately be used to differentiate those different solid forms from each other. For example, differences in physical properties such as solubility, stability, and biopharmaceutical properties such as $C_{max}$, $T_{max}$, bioavailability, are also of importance when describing the solid state of a compound.

Therefore, in the development of the compound 4-chloro-3-(2-(2-((4-((3S,5R)-3,5-dimethyl piperazin-1-yl)phenyl)amino)pyrimidin-5-yl)ethyl)-5-methoxy-N-methylbenzamide, studies on the salts of the compound and the crystalline forms thereof are needed.

SUMMARY OF THE INVENTION

Upon extensive explorations and research, the inventors have found that the compound 4-chloro-3-(2-(2-((4-((3S,5R)-3,5-dimethylpiperazin-1-yl)phenyl)amino)pyrimidin-5-yl)ethyl)-5-methoxy-N-methylbenzamide (also called "Compound 78" in the context of the present invention) can be prepared into various pharmaceutically acceptable salts represented by Formula A. As compared with Compound 78 in free form, the salt of Formula A (such as hemitartrate) has significantly increased solubility, which is beneficial for improving the pharmacokinetic characteristics and in vivo bioavailability of Compound 78. The inventors have also found that salt of Formula A can exist in different crystalline forms, and can form solvates with certain solvents. The inventors have made extensive studies on the polymorphs of the salt of Formula A and have finally prepared and determined the crystalline forms which meet the requirements of pharmaceutical use. Based on these studies, the present invention provides the pharmaceutically acceptable salts of Compound 78 represented by Formula A and the various crystalline forms thereof, such as Form A-III, Form B-II, Form B-III, and Form C-I.

In one aspect, the present invention provides the pharmaceutically acceptable salts of 4-chloro-3-(2-(2-((4-((3S,5R)-

3,5-dimethylpiperazin-1-yl)phenyl)amino)pyrimidin-5-yl) ethyl)-5-methoxy-N-methylbenzamide represented by Formula A:

Formula A

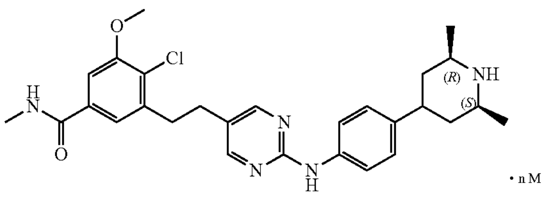

wherein n is 0.5 or 1 and M is the pharmaceutically acceptable acid.

In an embodiment, the present invention provides the salt of Formula A, wherein M is hydrochloric acid, tartaric acid, or p-toluenesulfonic acid.

In another embodiment, the present invention provides the salt of Formula A, wherein n is 1 and M is hydrochloric acid (also called monohydrochloride of Compound 78), n is 0.5 and M is tartaric acid (also called hemitartrate of Compound 78), or n is 1 and M is p-toluenesulfonic acid (also called mono p-tosylate of Compound 78).

In another embodiment, the present invention provides the salt of Formula A, wherein n is 1 and M is hydrochloric acid, which is Form A-III (also called Form A-III of monohydrochloride of Compound 78, briefly called Form A-III).

In another embodiment, the present invention provides the salt of Formula A, wherein n is 0.5 and M is tartaric acid, which is Form B-II (also called Form B-II of hemitartrate of Compound 78, briefly called Form B-II).

In another embodiment, the present invention provides the salt of Formula A, wherein n is 0.5 and M is tartaric acid, which is Form B-III (also called Form B-III of hemitartrate of Compound 78, briefly called Form B-III).

In another embodiment, the present invention provides the salt of Formula A, wherein n is 1 and M is p-toluenesulfonic acid, which is Form C-I (also called Form C-I of mono p-tosylate of Compound 78, briefly called Form C-I).

In another aspect, the present invention provides the methods for preparing the salt of Formula A and the crystalline forms thereof (such as Form A-III, Form B-II, Form B-III, or Form C-I), which are reproducible and easy to operate.

In another aspect, the present invention provides a pharmaceutical composition comprising an effective amount of the salt of Formula A and the crystalline forms thereof (such as Form A-III, Form B-II, Form B-III, or Form C-I), and optionally a pharmaceutically acceptable carrier.

In another aspect, the present invention further provides a method of preventing or treating a disease responsive to inhibition of FGFR activity, such as cancer, comprising administering to a subject in need thereof an effective amount of the salt of Formula A and the crystalline forms thereof, such as Form A-III, Form B-II, Form B-III, or Form C-I.

In another aspect, the present invention further provides use of the salt of Formula A and the crystalline forms thereof (such as Form A-III, Form B-II, Form B-III, or Form C-I) in the manufacture of a medicament for treating a disease responsive to inhibition of FGFR activity, such as cancer.

In another aspect, the present invention provides the salt of Formula A and the crystalline forms thereof (such as Form A-III, Form B-II, Form B-III, or Form C-I) for use in therapy.

In one embodiment, the present invention provides the salt of Formula A and the crystalline forms thereof (such as Form A-III, Form B-II, Form B-III, or Form C-I) for use in the treatment of a disease responsive to inhibition of FGFR activity, such as cancer.

Said cancer includes, but not limited to, lung cancer (such as squamous non-small cell lung cancer and small cell lung cancer), gastric cancer, liver cancer, breast cancer, ovarian cancer, endometrial cancer, bladder cancer, urothelial cancer, esophageal cancer, biliary tract cancer, colon cancer, rectal cancer, head and neck cancer, cervical cancer, pancreatic cancer, adrenal cancer, glioma, mesothelioma, and hematologic malignancy (such as myeloproliferative neoplasm).

DETAILED DESCRIPTION OF THE INVENTION

Definitions

Figure 1:
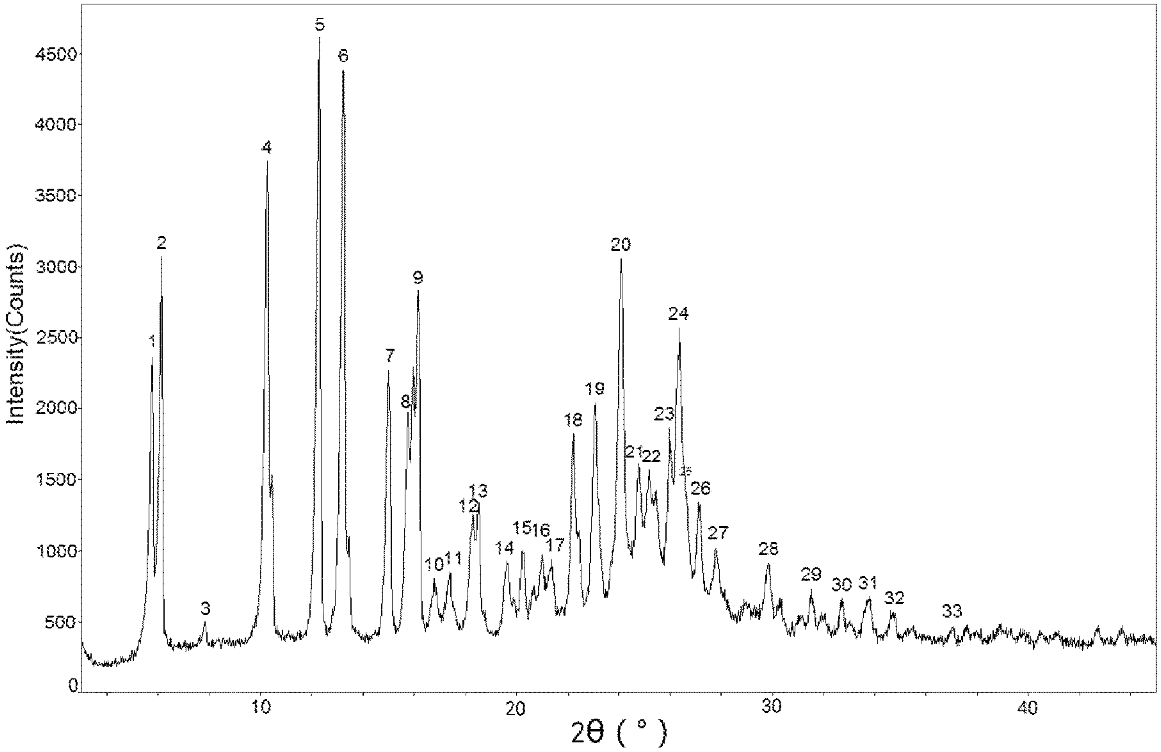
FIG. 1 shows an X-ray powder diffraction pattern of Form A-III of monohydrochloride of Compound 78, wherein the horizontal axis (X-axis) plots the diffraction angle 2 theta, and the vertical axis (Y-axis) plots the diffraction intensity.

Unless indicated otherwise, the following terms as used in the present application (including the specification and the claims) have the meanings as set forth below. It is to be noted that the singular forms in the specification and the claims include plural references, unless clearly indicated otherwise.

The terms "salt(s) of the present invention", "pharmaceutically acceptable salt(s) of 4-chloro-3-(2-(2-((4-((3S,5R)-3,5-dimethylpiperazin-1-yl)phenyl)amino)pyrimidin-5-yl)ethyl)-5-methoxy-N-methylbenzamide", "salt(s) of 4-chloro-3-(2-(2-((4-((3S,5R)-3,5-dimethylpiperazin-1-yl)phenyl)amino)pyrimidin-5-yl)ethyl)-5-methoxy-N-methylbenzamide", "salt(s) of Compound 78", "pharmaceutically acceptable salt(s) of Compound 78", and "salt(s) of Formula A" as used herein may be used interchangeably, and all refer to the salt of Formula A as described herein, i.e., an acid addition salt formed by Compound 78 and a "pharmaceutically acceptable acid" as described herein.

The term "crystalline form of the present invention" as used herein refers to Form A-III of monohydrochloride of Compound 78, Form B-II of hemitartrate of Compound 78, Form B-III of hemitartrate of Compound 78 or Form C-I of mono p-tosylate of Compound 78, or a mixture of any ratio thereof.

The terms "form", "crystal form", "crystalline form" and "polymorph" as used herein may be used interchangeably.

The term "pharmaceutically acceptable acid" as used herein refers to an acid that can form acid addition salt with Compound 78, and has no undesirable properties for application to animals or human, including, but not limited to inorganic acid, such as hydrochloric acid, hydrobromic acid, phosphoric acid, phosphorous acid, sulfuric acid, sulfurous acid, nitric acid, and the like; as well as organic acid, such as malic acid, maleic acid, mandelic acid, fumaric acid, tartaric acid, succinic acid, citric acid, aspartic acid, glutamic acid, 2-hydroxy-2-phenylpropionic acid, gluconic acid, lactic acid, camphorsulfonic acid, methanesulfonic acid, ethylsulfonic acid, naphthalenesulfonic acid, p-toluenesulfonic acid, 2-hydroxyethanesulfonic acid, β-hydroxybutyric acid, benzoic acid, salicylic acid, acetic acid, propionic acid, butyric acid, pentanoic acid, hexanoic acid, stearic acid, $HOOC-(CH_2)_n-COOH$ (wherein n is 0-4), and the like.

The term "organic acid ester with not more than eight carbon atoms" as used herein refers to $R_1COOR_2$, wherein $R_1$ and $R_2$ are independently saturated or unsaturated, straight or branched hydrocarbon radical, and the total number of the carbon atoms of $R_1$ and $R_2$ is less than or equal to 7; preferably, $R_1$ and $R_2$ are independently saturated, straight or branched hydrocarbon radical, and the total number of the carbon atoms of $R_1$ and $R_2$ is 1, 2, 3, 4, 5, 6, or 7. Examples of organic acid ester with not more than eight carbon atoms include but not limited to, methyl acetate, ethyl acetate, n-propyl acetate.

When the term "about" as used herein is used in conjunction with a numerical value, it modifies that given numerical value above or below the stated value by a variance of 10%. For example, about 50% means a range from 45% to 55%.

The term "substantially pure" as used herein means that the purity of said form is at least 50%, at least 60%, at least 70%, preferably at least 80%, more preferably at least 90%, even more preferably at least 95%, by weight. For example, the purity of said form is 95%, 96%, 97%, 98%, 99% or 100%, by weight.

The term "substantially free of other forms" as used herein means that the content of said other forms is less than 50%, preferably less than 40%, preferably less than 30%, preferably less than 20%, preferably less than 10%, preferably less than 5%, preferably less than 1%, by weight, based on the total weight of the forms.

The term "solution" as used herein means a homogeneous phase mixture of one or more solutes in one or more solvents.

The term "dissolution solvent" as used herein refers to an organic solvent in which a substance can be dissolved completely or partially under an appropriate condition. The term "anti-dissolution solvent" as used herein refers to any appropriate organic solvent in which the substance has less solubility than in the dissolution solvent.

The term "water miscible organic solvent" as used herein refers to an organic solvent that can be miscible with water in any proportion. Examples include but not limited to $C_{1-6}$ alkanol, acetone, tetrahydrofuran, acetonitrile, dioxane, N,N-dimethylformamide, N,N-dimethylacetamide, dimethylsulfoxide, and the like.

The term "$C_{1-6}$ alkanol" as used herein refers to a fully saturated straight or branched alkyl alcohol having 1, 2, 3, 4, 5 or 6 carbon atoms. Examples include but not limited to methanol, ethanol, n-propanol, i-propanol, n-butanol, i-butanol, t-butanol, n-pentanol, i-pentanol, n-hexanol, and the like.

The term "effective amount" as used herein refers to an amount of the salt of the present invention or the crystalline form of the present invention effective to inhibit FGFR activity in vitro or effective to prevent or treat a disease responsive to inhibition of FGFR activity after administering to a subject. The effective amount of the salt of the present invention or the crystalline form of the present invention may vary with various factors, such as the specific salt type that is used, disease to be treated and the severity thereof, age and health status of the subject, administration route and form, judgement of the attending physician or a veterinary practitioner, and so on.

The term "disease responsive to inhibition of FGFR activity" as used herein refers to a disease that can be prevented or treated by inhibiting FGFR activity, such as cancer, including, but not limited to, lung cancer (such as squamous non-small cell lung cancer and small cell lung cancer), gastric cancer, liver cancer, breast cancer, ovarian cancer, endometrial cancer, bladder cancer, urothelial cancer, esophageal cancer, biliary tract cancer, colon cancer, rectal cancer, head and neck cancer, cervical cancer, pancreatic cancer, adrenal cancer, glioma, mesothelioma, and hematologic malignancy (such as myeloproliferative neoplasm).

The term "subject" as used herein means mammals and non-mammals. Mammals means any member of the mammalia class including, but not limited to, humans; non-human primates such as chimpanzees and other apes and monkey species; farm animals such as cattle, horses, sheep, goats, and pigs; domestic animals such as rabbits, dogs, and cats; laboratory animals including rodents, such as rats, mice, and guinea pigs; and the like. Examples of non-mammals include, but not limited to, birds, and the like. The term "subject" does not denote a specific age or sex.

The term "treat", "treating" or "treatment" as used herein refers to the alleviation of undesired physiological changes or disorders, such as the development or spread of cancer. For the purpose of the present invention, beneficial or desired clinical results include, but not limited to, remission of symptoms, reduction of severity of a disease, stabilization of a disease, and slowing the progress of a disease. The term "treat", "treating" or "treatment" also means longer survival compared to subjects that do not receive the treatment.

The term "prevent", "preventing" or "prevention" as used herein refers to preventing or postponing the development of a disease in a subject that has a risk of suffering from the disease.

EMBODIMENTS

Embodiment 1. A salt of Formula A:

Formula A

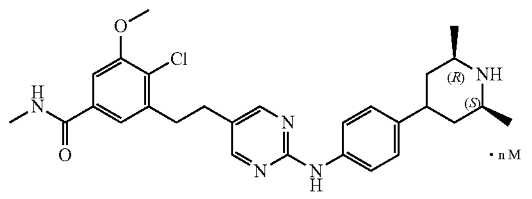

wherein n is 0.5 or 1; and M is a pharmaceutically acceptable acid.

Embodiment 2. The salt of Formula A according to embodiment 1, wherein M is hydrochloric acid, tartaric acid, or p-toluenesulfonic acid.

Embodiment 3. The salt of Formula A according to embodiment 2, wherein n is 1 and M is hydrochloric acid; n is 0.5 and M is tartaric acid; or n is 1 and M is p-toluenesulfonic acid.

Embodiment 4. The salt of Formula A according to embodiment 3, wherein n is 1 and M is hydrochloric acid, and the salt is Form A-III having the X-ray powder diffraction characteristic diffraction angles (2θ) of 5.8±0.2°, 6.2±0.2°, 12.3±0.2°, 13.3±0.2°, 23.1±0.2°, and 24.1±0.2°; preferably, said Form A-III has the X-ray powder diffraction characteristic diffraction angles (2θ) of 5.8±0.2°, 6.2±0.2°, 10.3±0.2°, 12.3±0.2°, 13.3±0.2°, 15.0±0.2°, 16.2±0.2°, 22.2±0.2°, 23.1±0.2°, 24.1±0.2°, and 26.4±0.2°;

more preferably, said Form A-III has the X-ray powder diffraction characteristic diffraction angles (2θ) of 5.8±0.2°, 6.2±0.2°, 10.3±0.2°, 12.3±0.2°, 13.3±0.2°, 15.0±0.2°, 15.8±0.2°, 16.2±0.2°, 18.3±0.2°, 18.5±0.2°, 20.2±0.2°, 22.2±0.2°, 23.1±0.2°, 24.1±0.2°, 26.4±0.2°, 27.1±0.2°, and 27.8±0.2°;

further preferably, said Form A-III has the X-ray powder diffraction characteristic diffraction angles (2θ) of 5.8±0.2°, 6.2±0.2°, 7.9±0.2°, 10.3±0.2°, 12.3±0.2°, 13.3±0.2°, 15.0±0.2°, 15.8±0.2°, 16.2±0.2°, 16.8±0.2°, 17.4±0.2°, 18.3±0.2°, 18.5±0.2°, 19.6±0.2°, 20.2±0.2°, 21.0±0.2°, 22.2±0.2°, 23.1±0.2°, 24.1±0.2°, 24.8±0.2°, 26.4±0.2°, 27.1±0.2°, and 27.8±0.2°;

most preferably, said Form A-III has the X-ray powder diffraction pattern as shown in FIG. 1.

Embodiment 5. The salt of Formula A according to embodiment 4, wherein said Form A-III has the differential scanning calorimetry (DSC) curve having an endothermic peak at about 290.2-295.4° C.

Figure 4:
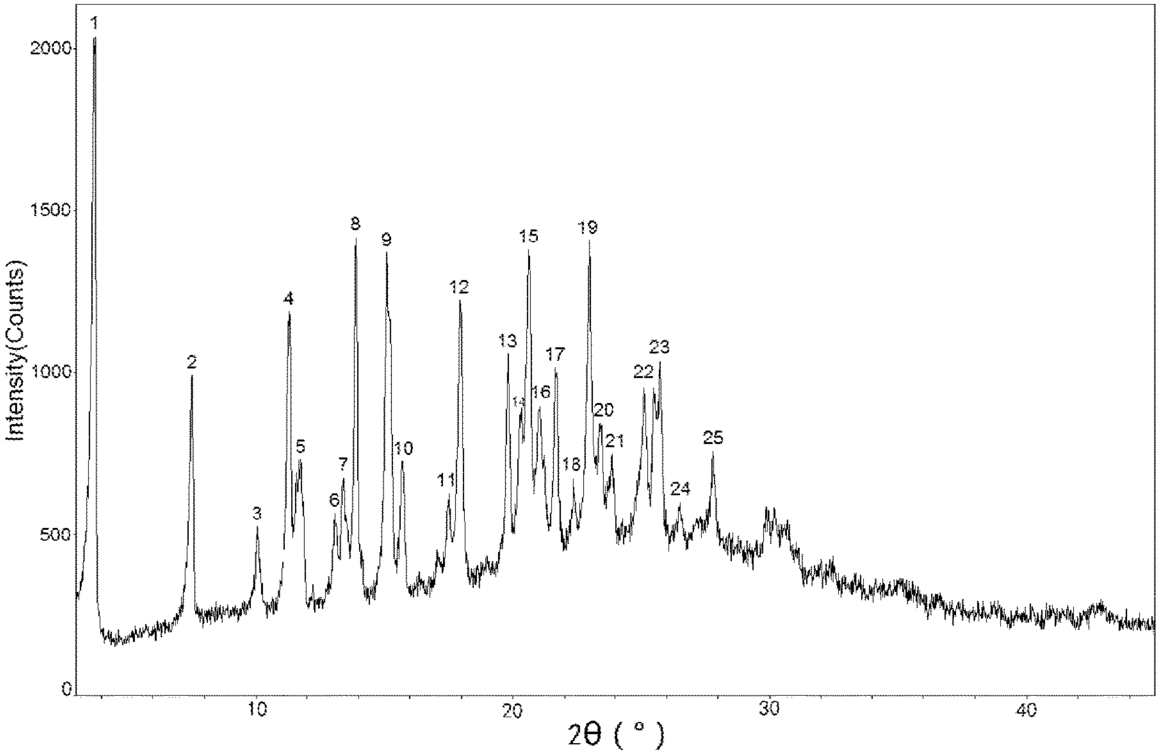
FIG. 4 shows an X-ray powder diffraction pattern of Form B-II of hemitartrate of Compound 78, wherein the horizontal axis (X-axis) plots the diffraction angle 2 theta, and the vertical axis (Y-axis) plots the diffraction intensity.

Embodiment 6. The salt of Formula A according to embodiment 3, wherein n is 0.5 and M is tartaric acid, and the salt is Form B-II having the X-ray powder diffraction characteristic diffraction angles (2θ) of 7.5±0.2°, 11.3±0.2°, 13.9±0.2°, 15.1±0.2°, 18.0±0.2°, and 20.6±0.2°; preferably, said Form B-II has the X-ray powder diffraction characteristic diffraction angles (2θ) of 3.8±0.2°, 7.5±0.2°, 11.3±0.2°, 13.9±0.2°, 15.1±0.2°, 15.7±0.2°, 18.0±0.2°, 19.8±0.2°, 20.6±0.2°, 21.7±0.2°, and 23.0±0.2°;

more preferably, said Form B-II has the X-ray powder diffraction characteristic diffraction angles (2θ) of 3.8±0.2°, 7.5±0.2°, 10.1±0.2°, 11.3±0.2°, 13.4±0.2°, 13.9±0.2°, 15.1±0.2°, 15.7±0.2°, 18.0±0.2°, 19.8±0.2°, 20.6±0.2°, 21.7±0.2°, 23.0±0.2°, 25.1±0.2°, and 27.8±0.2°;

further preferably, said Form B-II has the X-ray powder diffraction characteristic diffraction angles (2θ) of 3.8±0.2°, 7.5±0.2°, 10.1±0.2°, 11.3±0.2°, 11.8±0.2°, 13.1±0.2°, 13.4±0.2°, 13.9±0.2°, 15.1±0.2°, 15.7±0.2°, 18.0±0.2°, 19.8±0.2°, 20.6±0.2°, 21.1±0.2°, 21.7±0.2°, 23.0±0.2°, 25.1±0.2°, and 27.8±0.2°;

most preferably, said Form B-II has the X-ray powder diffraction pattern as shown in FIG. 4.

Embodiment 7. The salt of Formula A according to embodiment 6, wherein said Form B-II has the differential scanning calorimetry (DSC) curve having endothermic peaks at about 54.8-92.2° C., 166.9-174.4° C., and 263.3-265.3° C., and an exothermic peak at about 194.2-202.7° C.

Figure 6:
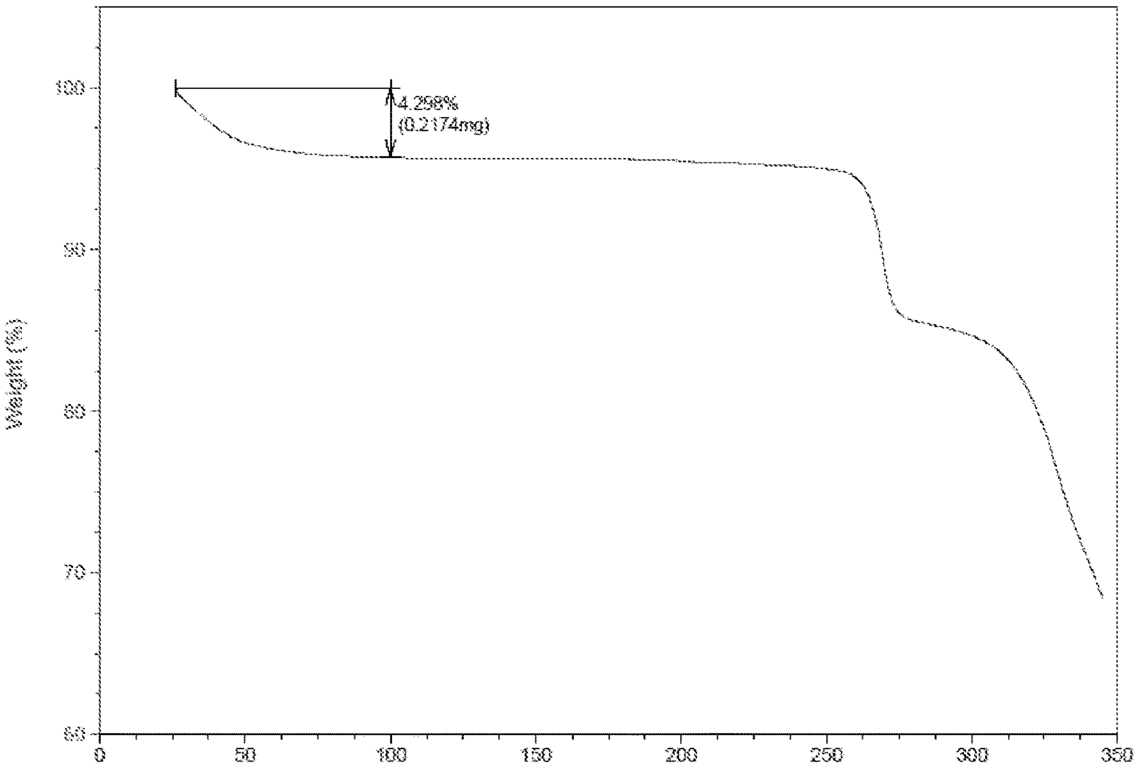
FIG. 6 shows a thermogravimetry (TG) curve of Form B-II of hemitartrate of Compound 78, wherein the horizontal axis (X-axis) plots the temperature (° C.), and the vertical axis (Y-axis) plots the weight percentage (%).

Embodiment 8. The salt of Formula A according to any one of embodiments 6-7, wherein said Form B-II has a thermogravimetric analysis (TGA) curve as shown in FIG. 6, indicating a weight loss of about 4.3% in the range from 30° C. to 100° C.

Figure 7:
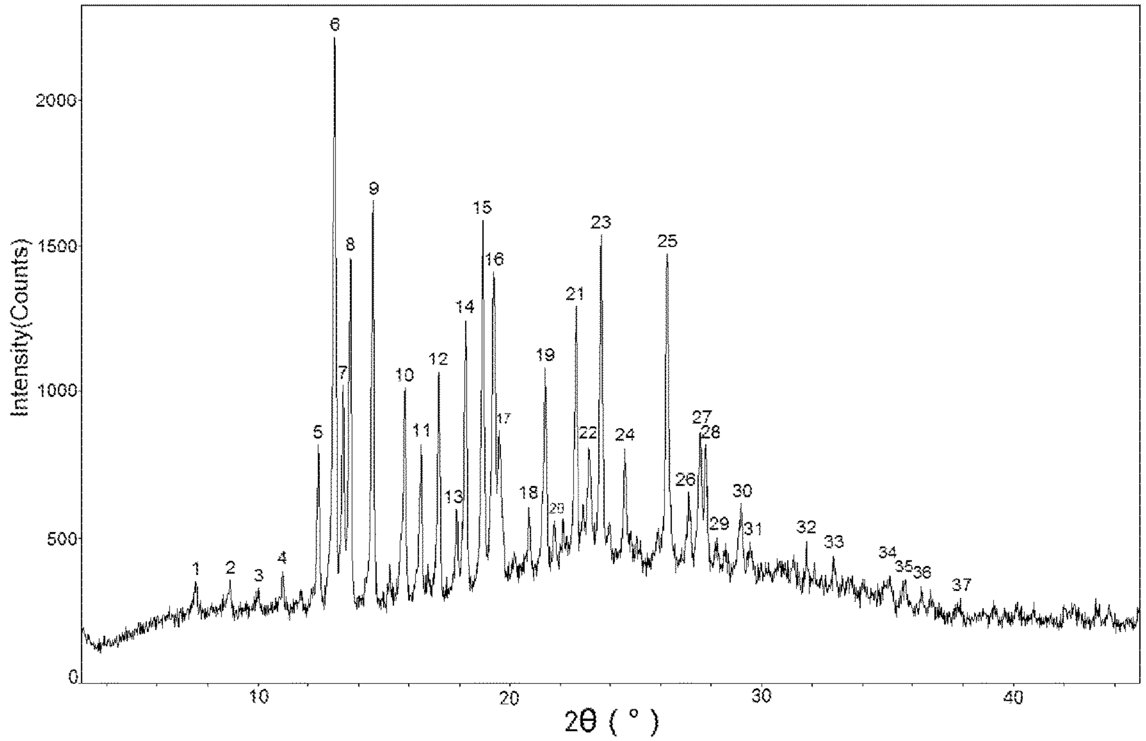
FIG. 7 shows an X-ray powder diffraction pattern of Form B-III of hemitartrate of Compound 78, wherein the horizontal axis (X-axis) plots the diffraction angle 2 theta, and the vertical axis (Y-axis) plots the diffraction intensity.

Embodiment 9. The salt of Formula A according to embodiment 3, wherein n is 0.5 and M is tartaric acid, and the salt is Form B-III having the X-ray powder diffraction characteristic diffraction angles (2θ) of 13.1±0.2°, 14.6±0.2°, 18.3±0.2°, 18.9±0.2°, 19.4±0.2°, and 26.3±0.2°;

preferably, said Form B-III has the X-ray powder diffraction characteristic diffraction angles (2θ) of 12.4±0.2°, 13.1±0.2°, 13.7±0.2°, 14.6±0.2°, 16.5±0.2°, 18.3±0.2°, 18.9±0.2°, 19.4±0.2°, 21.4±0.2°, 22.6±0.2°, 23.7±0.2°, and 26.3±0.2°;

more preferably, said Form B-III has the X-ray powder diffraction characteristic diffraction angles (2θ) of 7.6±0.2°, 8.9±0.2°, 10.0±0.2°, 11.0±0.2°, 12.4±0.2°, 13.1±0.2°, 13.4±0.2°, 13.7±0.2°, 14.6±0.2°, 15.9±0.2°, 16.5±0.2°, 18.3±0.2°, 18.9±0.2°, 19.4±0.2°, 21.4±0.2°, 22.6±0.2°, 23.7±0.2°, and 26.3±0.2°;

further preferably, said Form B-III has the X-ray powder diffraction characteristic diffraction angles (2θ) of 7.6±0.2°, 8.9±0.2°, 10.0±0.2°, 11.0±0.2°, 12.4±0.2°, 13.1±0.2°, 13.4±0.2°, 13.7±0.2°, 14.6±0.2°, 15.9±0.2°, 16.5±0.2°, 17.2±0.2°, 18.3±0.2°, 18.9±0.2°, 19.4±0.2°, 19.6±0.2°, 21.4±0.2°, 22.6±0.2°, 23.7±0.2°, 24.6±0.2°, 26.3±0.2°, 27.6±0.2°, and 29.2±0.2°; most preferably, said Form B-III has the X-ray powder diffraction pattern as shown in FIG. 7.

Embodiment 10. The salt of Formula A according to embodiment 9, wherein said Form B-III has the differential scanning calorimetry (DSC) curve having an endothermic peak at about 269.2-271.3° C.

Figure 9:
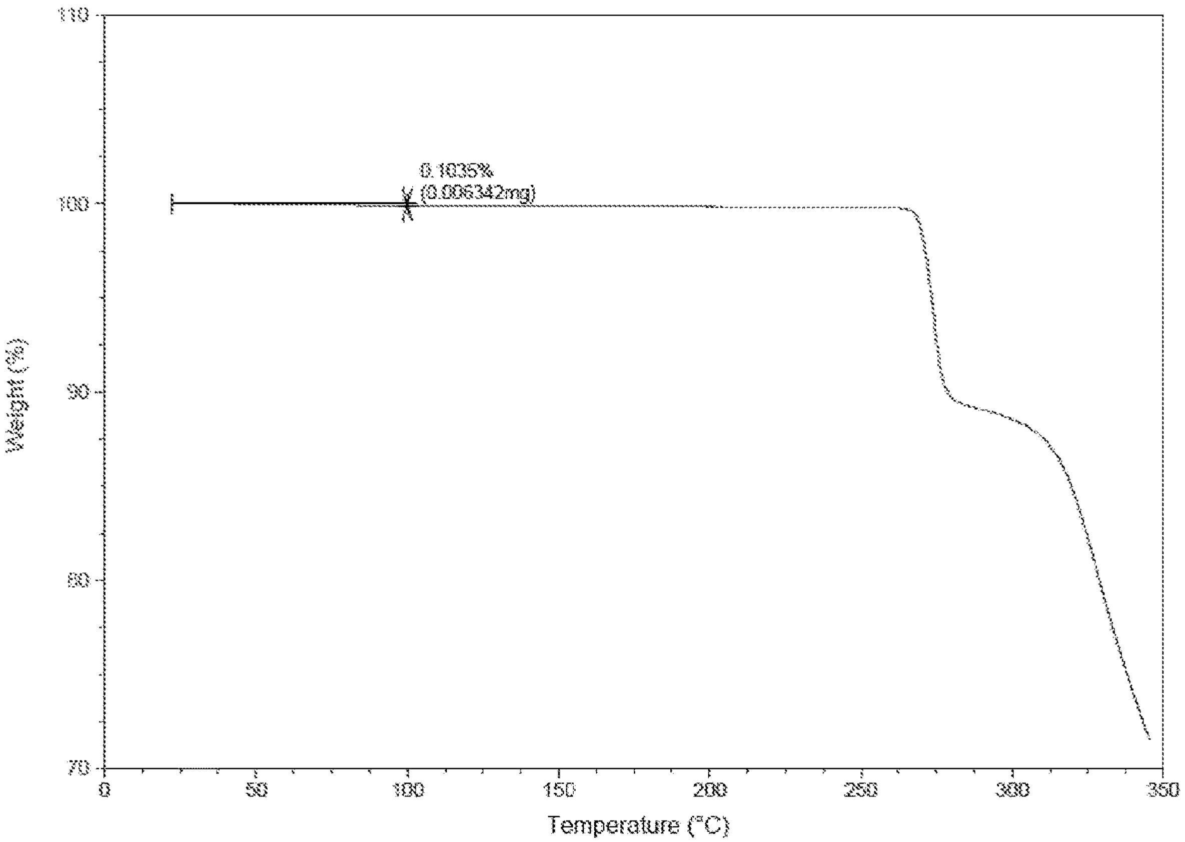
FIG. 9 shows a thermogravimetry (TG) curve of Form B-III of hemitartrate of Compound 78, wherein the horizontal axis (X-axis) plots the temperature (° C.), and the vertical axis (Y-axis) plots the weight percentage (%).

Embodiment 11. The salt of Formula A according to any one of embodiments 9-10, wherein said Form B-III has a thermogravimetric analysis (TGA) curve as shown in FIG. 9.

Figure 12:
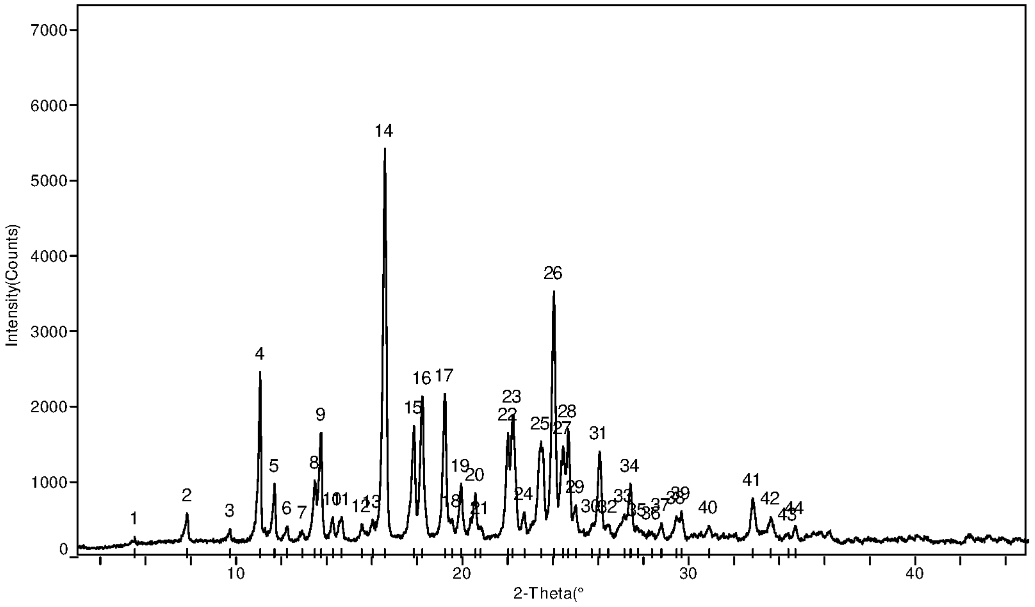
FIG. 12 shows an X-ray powder diffraction pattern of Form C-I of mono p-tosylate of Compound 78, wherein the horizontal axis (X-axis) plots the diffraction angle 2 theta, and the vertical axis (Y-axis) plots the diffraction intensity.

Embodiment 12. The salt of Formula A according to embodiment 3, wherein n is 1 and M is p-toluenesulfonic acid, and the salt is Form C-I having the X-ray powder diffraction characteristic diffraction angles (2θ) of 7.8±0.2°, 11.1±0.2°, 11.7±0.2°, 16.6±0.2°, 17.9±0.2°, 18.2±0.2°, 19.2±0.2°, and 24.0±0.2°;

preferably, said Form C-I has the X-ray powder diffraction characteristic diffraction angles (2θ) of 5.5±0.2°, 7.8±0.2°, 9.7±0.2°, 11.1±0.2°, 11.7±0.2°, 13.8±0.2°, 14.3±0.2°, 16.6±0.2°, 17.9±0.2°, 18.2±0.2°, 19.2±0.2°, 22.2±0.2°, 24.0±0.2°, and 26.1±0.2°;

more preferably, said Form C-I has the X-ray powder diffraction characteristic diffraction angles (2θ) of 5.5±0.2°, 7.8±0.2°, 9.7±0.2°, 11.1±0.2°, 11.7±0.2°, 13.5±0.2°, 13.8±0.2°, 14.3±0.2°, 14.7±0.2°, 16.6±0.2°, 17.9±0.2°, 18.2±0.2°, 19.2±0.2°, 20.0±0.2°, 20.6±0.2°, 22.2±0.2°, 24.0±0.2°, 26.1±0.2°, and 27.4±0.2°;

further preferably, said Form C-I has the X-ray powder diffraction characteristic diffraction angles (2θ) of 5.5±0.2°, 7.8±0.2°, 9.7±0.2°, 11.1±0.2°, 11.7±0.2°, 12.2±0.2°, 12.9±0.2°, 13.5±0.2°, 13.8±0.2°, 14.3±0.2°, 14.7±0.2°, 16.6±0.2°, 17.9±0.2°, 18.2±0.2°, 19.2±0.2°, 20.0±0.2°, 20.6±0.2°, 22.2±0.2°, 23.5±0.2°, 24.0±0.2°, 25.0±0.2°, 26.1±0.2°, 27.4±0.2°, and 32.8±0.2°; most preferably, said Form C-I has the X-ray powder diffraction pattern as shown in FIG. 12.

Embodiment 13. The salt of Formula A according to embodiment 12, wherein said Form C-I has the differential scanning calorimetry (DSC) curve having an endothermic peak at about 289.77-291.04° C.

Figure 14:
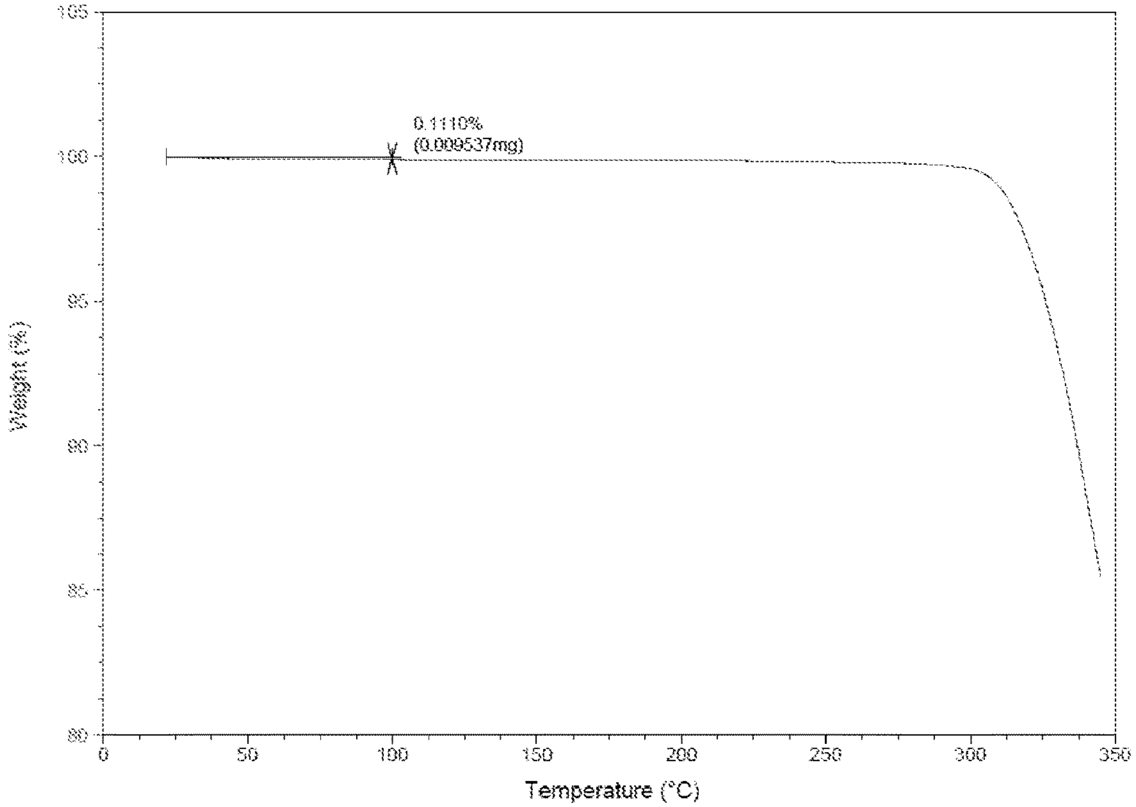
FIG. 14 shows a thermogravimetry (TG) curve of Form C-I of mono p-tosylate of Compound 78, wherein the horizontal axis (X-axis) plots the temperature (° C.), and the vertical axis (Y-axis) plots the weight percentage (%).

Embodiment 14. The salt of Formula A according to any one of embodiments 12-13, wherein said Form C-I has a thermogravimetric analysis (TGA) curve as shown in FIG. 14.

Embodiment 15. A pharmaceutical composition, comprising an effective amount of the salt of Formula A according to any one of embodiments 1-14, and optionally a pharmaceutically acceptable carrier.

Embodiment 16. A method of preventing or treating a disease responsive to inhibition of FGFR activity, comprising administering to a subject in need thereof an effective amount of the salt of Formula A according to any one of embodiments 1-14.

Embodiment 17. Use of the salt of Formula A according to any one of embodiments 1-14 in the manufacture of a medicament for preventing or treating a disease responsive to inhibition of FGFR activity, such as cancer.

Embodiment 18. The use according to embodiment 17, wherein said cancer is selected from lung cancer (such as squamous non-small cell lung cancer and small cell lung cancer), gastric cancer, liver cancer, breast cancer, ovarian cancer, endometrial cancer, bladder cancer, urothelial cancer, esophageal cancer, biliary tract cancer, colon cancer, rectal cancer, head and neck cancer, cervical cancer, pancreatic cancer, adrenal cancer, glioma, mesothelioma, and hematologic malignancy (such as myeloproliferative neoplasm).

Embodiment 19. The salt of Formula A according to any one of embodiments 1-14 for use in therapy.

Embodiment 20. The salt of Formula A according to any one of embodiments 1-14 for use in the treatment of a disease responsive to inhibition of FGFR activity, such as cancer.

Embodiment 21. The salt of Formula A according to embodiment 20, wherein said cancer is selected from lung cancer (such as squamous non-small cell lung cancer and small cell lung cancer), gastric cancer, liver cancer, breast cancer, ovarian cancer, endometrial cancer, bladder cancer, urothelial cancer, esophageal cancer, biliary tract cancer, colon cancer, rectal cancer, head and neck cancer, cervical cancer, pancreatic cancer, adrenal cancer, glioma, mesothelioma, and hematologic malignancy (such as myeloproliferative neoplasm).

Embodiment 22. A method for preparing the salt of Formula A according to any one of embodiments 4-5, comprising:

(1) mixing the compound 4-chloro-3-(2-(2-((4-((3S,5R)-3,5-dimethylpiperazin-1-yl) phenyl)amino)pyrimidin-5-yl)ethyl)-5-methoxy-N-methylbenzamide with hydrochloric acid in a dissolution solvent or in a mixed solvent consisting of water miscible organic solvent and water under heating and stirring for reacting to form a salt;

(2) cooling the reaction obtained in step (1) to precipitate the solid sufficiently;

(3) isolating the precipitated solid as Form A-III;

(4) optionally drying the solid obtained in step (3).

Embodiment 23. The method according to embodiment 22, wherein said hydrochloric acid is concentrated hydrochloric acid with the concentration of 36%-38% by weight.

Embodiment 24. The method according to any one of embodiments 22-23, wherein the molar ratio of said hydrochloric acid to said compound 4-chloro-3-(2-(2-((4-((3S, 5R)-3,5-dimethylpiperazin-1-yl)phenyl)amino)pyrimidin-5-yl)ethyl)-5-methoxy-N-methylbenzamide is not less than about 1:1, such as is about 1:1 or 1.2:1.

Embodiment 25. The method according to any one of embodiments 22-24, wherein the ratio of the volume of said dissolution solvent or said mixed solvent to the weight of said compound 4-chloro-3-(2-(2-((4-((3S,5R)-3,5-dimethylpiperazin-1-yl)phenyl)amino)pyrimidin-5-yl)ethyl)-5-methoxy-N-methylbenzamide is not less than about 10 ml/g, such as is about 20 ml/g or about 60 ml/g.

Embodiment 26. The method according to any one of embodiments 22-25, wherein said dissolution solvent is selected from $C_{1-6}$ alkanol; preferably, said dissolution solvent is selected from methanol, ethanol, i-propanol, t-butanol, and the mixture thereof; more preferably, said dissolution solvent is ethanol.

Embodiment 27. The method according to any one of embodiments 22-26, wherein said water miscible organic solvent is selected from $C_{1-6}$ alkanol; preferably, said water miscible organic solvent is selected from methanol, ethanol, i-propanol, t-butanol, and the mixture thereof, more preferably, said water miscible organic solvent is selected from ethanol, i-propanol, and the mixture thereof.

Embodiment 28. The method according to any one of embodiments 22-27, wherein the volume percentage of said water miscible organic solvent in said mixed solvent is not more than about 95%; preferably, the volume percentage of said water miscible organic solvent in said mixed solvent is 95%, 90%, or 80%.

Embodiment 29. The method according to any one of embodiments 22-28, wherein in the optional step (4), the drying temperature is 50-80° C.

Embodiment 30. A method for preparing the salt of Formula A according to any one of embodiments 6-8, comprising:

(1) mixing the compound 4-chloro-3-(2-(2-((4-((3S,5R)-3,5-dimethylpiperazin-1-yl)phenyl) amino)pyrimidin-5-yl)ethyl)-5-methoxy-N-methylbenzamide with L-tartaric acid in ethanol under heating and stirring for reacting to form a salt;

(2) cooling the reaction obtained in step (1) to precipitate the solid sufficiently;

(3) isolating the precipitated solid as Form B-II;

(4) optionally drying the solid obtained in step (3).

Embodiment 31. The method according to embodiment 30, wherein the molar ratio of said L-tartaric acid to said compound 4-chloro-3-(2-(2-((4-((3S,5R)-3,5-dimethylpiperazin-1-yl) phenyl)amino)pyrimidin-5-yl)ethyl)-5-methoxy-N-methylbenzamide is not less than about 1:2, preferably, is about 4:5 or about 3.4:1.

Embodiment 32. The method according to any one of embodiments 30-31, wherein the ratio of the volume of said ethanol to the weight of said compound 4-chloro-3-(2-(2-((4-((3S,5R)-3,5-dimethylpiperazin-1-yl)phenyl)amino)pyrimidin-5-yl)ethyl)-5-methoxy-N-methylbenzamide is not less than about 10 ml/g, such as is about 72 ml/g or about 75 ml/g.

Embodiment 33. The method according to any one of embodiments 30-32, wherein in the optional step (4), the drying temperature is 50-85° C.

Embodiment 34. A method for preparing the salt of Formula A according to any one of embodiments 9-11, comprising:

(1) mixing the compound 4-chloro-3-(2-(2-((4-((3S,5R)-3,5-dimethylpiperazin-1-yl)phenyl) amino)pyrimidin-5-yl)ethyl)-5-methoxy-N-methylbenzamide with L-tartaric acid in a dissolution solvent, in water, or in a mixed solvent consisting of water miscible organic solvent and water under heating and stirring for reacting to form a salt, thereby obtaining the first solution; provided that said dissolution solvent is not the single solvent ethanol;

(2) optionally adding an anti-dissolution solvent into said first solution to obtain the second solution;

(3) cooling said first solution or second solution to precipitate the solid sufficiently;

(4) isolating the precipitated solid as Form B-III;

(5) optionally drying the solid obtained in step (4).

Embodiment 35. The method according to embodiment 34, wherein the molar ratio of said L-tartaric acid to said compound 4-chloro-3-(2-(2-((4-((3S,5R)-3,5-dimethylpiperazin-1-yl) phenyl)amino)pyrimidin-5-yl)ethyl)-5-methoxy-N-methylbenzamide is not less than about 1:1, preferably, the molar ratio is about 1:1 or about 1.5:1.

Embodiment 36. The method according to any one of embodiments 34-35, wherein the ratio of the volume of said dissolution solvent, said water, or said mixed solvent consisting of water miscible organic solvent and water to the weight of said compound 4-chloro-3-(2-(2-((4-((3S,5R)-3,5-dimethylpiperazin-1-yl)phenyl)amino)pyrimidin-5-yl) ethyl)-5-methoxy-N-methylbenzamide is not less than about 10 ml/g, such as is about 20 ml/g, about 30 ml/g, about 33 ml/g, about 50 ml/g, about 65 ml/g, about 98 ml/g, or about 286 ml/g.

Embodiment 37. The method according to any one of embodiments 34-36, wherein said dissolution solvent is selected from $C_{1-6}$ alkanol, acetone, toluene, organic acid ester with not more than eight carbon atoms, and the mixture thereof; preferably, said dissolution solvent is selected from methanol, ethanol, i-propanol, t-butanol, n-butanol, acetone, toluene, n-propyl acetate, ethyl acetate, and the mixture thereof; more preferably, said dissolution solvent is selected from methanol, ethanol, i-propanol, acetone, toluene, n-propyl acetate, ethyl acetate, and the mixture thereof.

Embodiment 38. The method according to embodiment 37, wherein said dissolution solvent is selected from a mixed solvent consisting of two solvents of methanol, ethanol, toluene, n-propyl acetate, and ethyl acetate, for example, n-propyl acetate/methanol (in the volume ratio of about 3:2), toluene/ethanol (in the volume ratio of about 1:1), or ethyl acetate/ethanol (in the volume ratio of about 11:15).

Embodiment 39. The method according to any one of embodiments 34-38, wherein said water miscible organic solvent is selected from $C_{1-6}$ alkanol, acetone, and the mixture thereof; preferably, said water miscible organic solvent is selected from methanol, ethanol, i-propanol, t-butanol, acetone, and the mixture thereof; more preferably, said water miscible organic solvent is selected from ethanol, i-propanol, acetone, and the mixture thereof.

Embodiment 40. The method according to any one of embodiments 34-39, wherein the volume percentage of said water miscible organic solvent in said mixed solvent is not more than about 95%, such as 95%, 90%, 80%.

Embodiment 41. The method according to any one of embodiments 34-40, wherein said anti-dissolution solvent is selected from toluene, organic acid ester with not more than eight carbon atoms, and the mixture thereof; preferably, said anti-dissolution solvent is selected from toluene, ethyl acetate, n-propyl acetate, and the mixture thereof; more preferably, said anti-dissolution solvent is selected from toluene, ethyl acetate, and the mixture thereof.

Embodiment 42. The method according to any one of embodiments 34-41, wherein in step (3), said cooling is cooling naturally or cooling at a controlled temperature.

Embodiment 43. The method according to any one of embodiments 34-42, wherein in step (5), the drying temperature is 50-85° C.

Embodiment 44. A method for preparing the salt of Formula A according to any one of embodiments 12-14, comprising:

(1) mixing the compound 4-chloro-3-(2-(2-((4-((3S,5R)-3,5-dimethylpiperazin-1-yl) phenyl)amino)pyrimidin-5-yl)ethyl)-5-methoxy-N-methylbenzamide with p-toluenesulfonic acid monohydrate in a mixed solvent consisting of water miscible organic solvent and water under heating and stirring for reacting to form a salt;

(2) cooling the reaction obtained in step (1) to precipitate the solid sufficiently;

(3) isolating the precipitated solid as Form C-I;

(4) optionally drying the solid obtained in step (3).

Embodiment 45. The method according to embodiment 44, wherein the molar ratio of said p-toluenesulfonic acid monohydrate to said compound 4-chloro-3-(2-(2-((4-((3S,5R)-3,5-dimethylpiperazin-1-yl)phenyl)amino)pyrimidin-5-yl)ethyl)-5-methoxy-N-methylbenzamide is not less than about 1:1, such as is about 1.5:1.

Embodiment 46. The method according to any one of embodiments 44-45, wherein the ratio of the volume of said mixed solvent consisting of water miscible organic solvent and water to the weight of said compound 4-chloro-3-(2-(2-((4-((3S,5R)-3,5-dimethylpiperazin-1-yl)phenyl) amino) pyrimidin-5-yl)ethyl)-5-methoxy-N-methylbenzamide in step (1) is not less than about 10 ml/g, such as is about 36 ml/g or about 43 ml/g.

Embodiment 47. The method according to any one of embodiments 44-46, wherein said water miscible organic solvent is selected from $C_{1-6}$ alkanol, acetone, and the mixture thereof; preferably, said water miscible organic solvent is selected from i-propanol, acetone, and the mixture thereof.

Embodiment 48. The method according to any one of embodiments 44-47, wherein the volume percentage of said water miscible organic solvent in said mixed solvent is not more than about 95%, such as is 80%.

Embodiment 49. The method according to any one of embodiments 44-48, wherein after the completion of the reaction in step (1), an anti-dissolution solvent (such as i-propanol) is added prior to step (2).

Embodiment 50. The method according to any one of embodiments 44-49, wherein in step (2), said cooling is cooling naturally or cooling at a controlled temperature.

Embodiment 51. The method according to any one of embodiments 44-50, wherein in the optional step (4), the drying temperature is 50-60° C.

The salts of the present invention and the crystalline forms of the present invention have the characteristics of good crystallinity, high solubility, low hygroscopicity, and good stability. The salts of the present invention and the crystalline forms of the present invention have good reproducibility and are easy to be scaled up with constant manufacture of high quality products to meet the quality requirements of drugs.

For example, Compound 78 in free form prepared according to Example 9 of WO2014/139465A1 is a yellow solid as an acicular crystal, while Form B-III of the present invention is a tabular crystal, which has smaller length diameter and better graininess than the acicular crystal, so it has smaller repose angle, that is, better flowability. These characteristics make Form B-III more advantageous to mix with excipients uniformly in subsequent formulation procedure, which can simplify the formulation process, improve production efficiency and save production cost.

Moreover, the salts of the present invention and the crystalline forms of the present invention have better solubility properties. For example, as compared to Compound 78 in free form, the salts of the present invention have smaller solubility difference at different pH values, which makes the solubility of the salts of the present invention in the body fluid with different pH values more stable. In addition, Form B-III of the present invention has higher solubility than Compound 78 in free form and other salts under gastric acid condition, which is beneficial to its rapid dissolution in the stomach. Meanwhile, the salts of the present invention and the crystalline forms of the present invention still have high and stable solubility under high pH condition of gastrointestinal tract, which is beneficial to its sufficient absorption, thus resulting in higher bioavailability, and which may also decrease the effects of food on drug absorption in vivo.

Form B-III of the present invention has low hygroscopicity and good stability, so it is especially convenient for Form B-III to be used in the manufacture, storage, transportation of formulations and in treatment of diseases.

In addition, the crystalline forms of the present invention have high purity and less solvent residue, which meet the quality requirements of bulk drug, such as ICH Q3A.

A person skilled in the art can verify the above advantages of the salts of the present invention and the crystalline forms of the present invention according to the methods known in the art, such as the test methods disclosed in the pharmacopoeias of various countries or the modifications thereof. For example, the crystalline forms of the present invention may be identified by X-ray powder diffraction, single crystal diffraction, Fourier Infrared Spectroscopy, differential scanning calorimetry, and/or thermogravimetric analysis.

It is known in the art that the peak intensity and/or positions in the X-ray powder diffraction pattern may vary with the different experiment conditions. For example, the measured 2θ value may be slightly different due to different instruments, different test conditions and/or preferential orientations. Furthermore, it is known that, the relative intensity values of the peaks are more susceptible than the peak positions to the test samples, e.g., crystal size in the sample, crystallization orientation effect, and the purity of the analyzed materials. Therefore, the deviation of the peak intensity may be up to about ±20% or greater. However, despite of experimental errors, instrument errors, preferential orientations and the like, a person skilled in the art, on the basis of the main peaks of X-ray powder diffraction and even further combined with other characterization data, can obtain sufficient information to identify Form A-III, Form B-II, Form B-III, and Form C-I.

Identification of Form A-III

The present invention provides Form A-III.

In some embodiments, Form A-III may be identified by X-ray powder diffraction. In some embodiments, the X-ray powder diffraction characteristic diffraction angles (2θ) of Form A-III include 5.8±0.2°, 6.2±0.2°, 12.3±0.2°, 13.3±0.2°, 23.1±0.2°, and 24.1±0.2°.

In some embodiments, the X-ray powder diffraction characteristic diffraction angles (2θ) of Form A-III include 5.8±0.2°, 6.2±0.2°, 10.3±0.2°, 12.3±0.2°, 13.3±0.2°, 15.0±0.2°, 16.2±0.2°, 22.2±0.2°, 23.1±0.2°, 24.1±0.2°, and 26.4±0.2°.

In some embodiments, the X-ray powder diffraction characteristic diffraction angles (2θ) of Form A-III include 5.8±0.2°, 6.2±0.2°, 10.3±0.2°, 12.3±0.2°, 13.3±0.2°, 15.0±0.2°, 15.8±0.2°, 16.2±0.2°, 18.3±0.2°, 18.5±0.2°, 20.2±0.2°, 22.2±0.2°, 23.1±0.2°, 24.1±0.2°, 26.4±0.2°, 27.1±0.2°, and 27.8±0.2°.

In some embodiments, the X-ray powder diffraction characteristic diffraction angles (2θ) of Form A-III include 5.8±0.2°, 6.2±0.2°, 7.9±0.2°, 10.3±0.2°, 12.3±0.2°, 13.3±0.2°, 15.0±0.2°, 15.8±0.2°, 16.2±0.2°, 16.8±0.2°, 17.4±0.2°, 18.3±0.2°, 18.5±0.2°, 19.6±0.2°, 20.2±0.2°, 21.0±0.2°, 22.2±0.2°, 23.1±0.2°, 24.1±0.2°, 24.8±0.2°, 26.4±0.2°, 27.1±0.2°, and 27.8±0.2°.

In some embodiments, the X-ray powder diffraction characteristic diffraction angles (2θ) of Form A-III include 5.8±0.2°, 6.2±0.2°, 7.9±0.2°, 10.3±0.2°, 12.3±0.2°, 13.3±0.2°, 15.0±0.2°, 15.8±0.2°, 16.2±0.2°, 16.8±0.2°, 17.4±0.2°, 18.3±0.2°, 18.5±0.2°, 19.6±0.2°, 20.2±0.2°, 21.0±0.2°, 21.4±0.2°, 22.2±0.2°, 23.1±0.2°, 24.1±0.2°, 24.8±0.2°, 25.2±0.2°, 26.0±0.2°, 26.4±0.2°, 27.1±0.2°, 27.8±0.2°, 29.8±0.2°, 31.5±0.2°, and 32.7±0.2°.

In some embodiments, Form A-III has the X-ray powder diffraction pattern as shown in FIG. 1.

Figure 2:
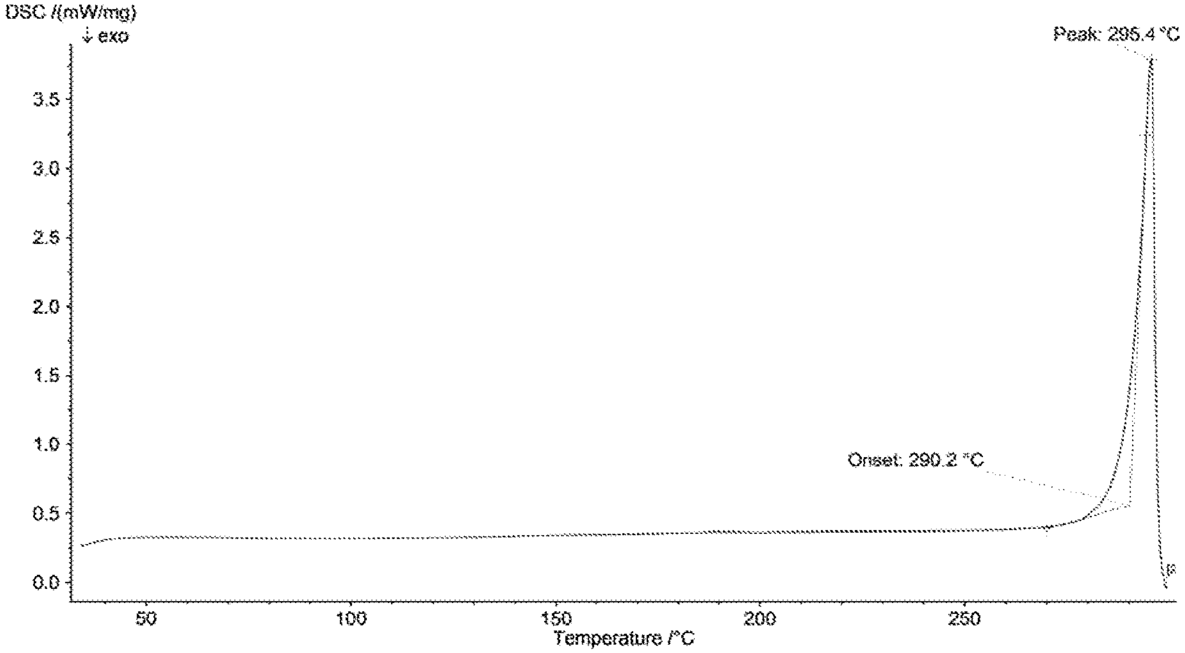
FIG. 2 shows a differential scanning calorimetry (DSC) curve of Form A-III of monohydrochloride of Compound 78, wherein the horizontal axis (X-axis) plots the temperature (° C.), and the vertical axis (Y-axis) plots the heat flow (mW).

In some embodiments, Form A-III may be characterized by differential scanning calorimetry (DSC). In some embodiments, Form A-III has a DSC curve as shown in FIG. 2. In the DSC curve, the endothermic peak of Form A-III is at about 290.2-295.4° C.

In some embodiments, Form A-III may be characterized by thermogravimetric analysis (TGA).

Figure 3:
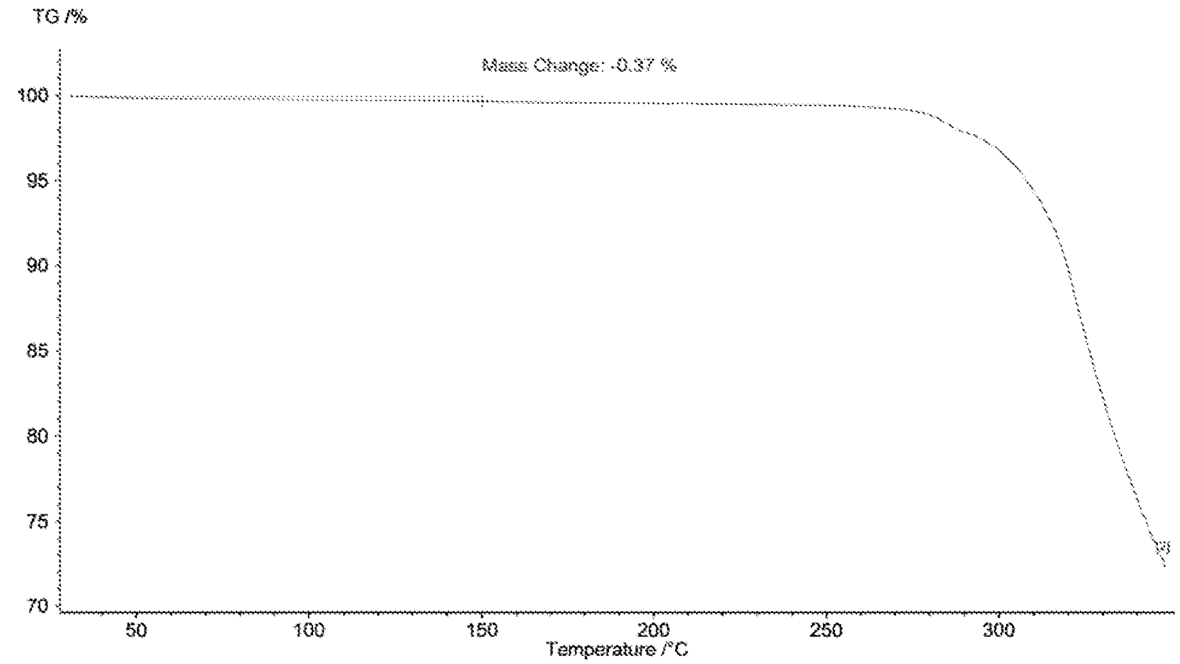
FIG. 3 shows a thermogravimetry (TG) curve of Form A-III of monohydrochloride of Compound 78, wherein the horizontal axis (X-axis) plots the temperature (° C.), and the vertical axis (Y-axis) plots the weight percentage (%).

In some embodiments, Form A-III has a TGA curve as shown in FIG. 3, indicating that Form A-III is anhydrous or neat.

In some embodiments, said Form A-III is substantially pure.

In some embodiments, said Form A-III is substantially free of other crystalline forms. For example, the content by weight of Form A-III is at least 99%, at least 95%, at least 90%, at least 80%, at least 70%, at least 60%, or at least 50%.

Methods for Preparing Form A-III The present invention provides a method for preparing Form A-III, comprising:

(1) mixing the compound 4-chloro-3-(2-(2-((4-((3S,5R)-3,5-dimethylpiperazin-1-yl) phenyl)amino)pyrimidin-5-yl)ethyl)-5-methoxy-N-methylbenzamide with hydrochloric acid in a dissolution solvent or in a mixed solvent consisting of water miscible organic solvent and water under heating and stirring for reacting to form a salt;

(2) cooling the reaction obtained in step (1) to precipitate the solid sufficiently;

(3) isolating the precipitated solid as Form A-III;

(4) optionally drying the solid obtained in step (3).

In some embodiments, said hydrochloric acid is concentrated hydrochloric acid with the concentration of 36%-38% by weight.

In some embodiments, the molar ratio of said hydrochloric acid to the compound 4-chloro-3-(2-(2-((4-((3S,5R)-3,5-dimethylpiperazin-1-yl)phenyl)amino)pyrimidin-5-yl) ethyl)-5-methoxy-N-methylbenzamide is not less than about 1:1. In some embodiments, said molar ratio is about 1:1. In some embodiments, said molar ratio is about 1.2:1.

In some embodiments, the ratio of the volume (ml) of said dissolution solvent or said mixed solvent to the weight (g) of the compound 4-chloro-3-(2-(2-((4-((3S,5R)-3,5-dimethylpiperazin-1-yl)phenyl)amino)pyrimidin-5-yl)ethyl)-5-methoxy-N-methylbenzamide is not less than about 10 ml/g, such as about 20 ml/g, about 60 ml/g, and the like.

In some embodiments, said dissolution solvent is selected from $C_{1-6}$ alkanol. In some embodiments, said dissolution solvent is selected from methanol, ethanol, i-propanol, t-butanol, and the mixture thereof. In some embodiments, said dissolution solvent is selected from ethanol.

In some embodiments, said water miscible organic solvent is selected from $C_{1-6}$ alkanol. In some embodiments, said water miscible organic solvent is selected from methanol, ethanol, i-propanol, t-butanol, and the mixture thereof. In some embodiments, said water miscible organic solvent is selected from ethanol, i-propanol, and the mixture thereof.

In some embodiments, the volume percentage of said water miscible organic solvent in said mixed solvent is not more than about 95%, for example, the volume percentage of said water miscible organic solvent in said mixed solvent is 95%, 90%, 80%, and the like.

In some embodiments, in said step (1), the heating temperature should not be higher than the 30 boiling point of the solvent system, such as 75-80° C., 75-85° C., and the like.

In some embodiments, in said step (2), said cooling is cooling naturally or cooling at a controlled temperature, and cooling to room temperature or lower temperature, such as 20-25° C., 15-25° C., and the like.

In some embodiments, in said step (2), after cooling, the reaction is stirred for 1-120 hours, such as 2 hours, 20 hours, and the like, to precipitate the solid sufficiently.

In some embodiments, in said optional step (4), the drying temperature and drying time can be 40 determined conventionally by a person skilled in the art, so that the solid is dried sufficiently and the desired crystalline form is maintained. In some embodiments, the drying temperature is 50-80° C., such as 60° C. In some embodiments, the drying time is 1-24 hours, such as 2 hours, 18 hours, and the like.

Identification of Form B-II

The present invention provides Form B-II.

In some embodiments, Form B-II may be identified by X-ray powder diffraction. In some embodiments, the X-ray powder diffraction characteristic diffraction angles (2θ) of Form B-II include 7.5±0.2°, 11.3±0.2°, 13.9±0.2°, 15.1±0.2°, 18.0±0.2°, and 20.6±0.2°.

In some embodiments, the X-ray powder diffraction characteristic diffraction angles (2θ) of Form B-II include 3.8±0.2°, 7.5±0.2°, 11.3±0.2°, 13.9±0.2°, 15.1±0.2°, 15.7±0.2°, 18.0±0.2°, 19.8±0.2°, 20.6±0.2°, 21.7±0.2°, and 23.0±0.2°.

In some embodiments, the X-ray powder diffraction characteristic diffraction angles (2θ) of Form B-II include 3.8±0.2°, 7.5±0.2°, 10.1±0.2°, 11.3±0.2°, 13.4±0.2°, 13.9±0.2°, 15.1±0.2°, 15.7±0.2°, 18.0±0.2°, 19.8±0.2°, 20.6±0.2°, 21.7±0.2°, 23.0±0.2°, 25.1±0.2°, and 27.8±0.2°.

In some embodiments, the X-ray powder diffraction characteristic diffraction angles (2θ) of Form B-II include 3.8±0.2°, 7.5±0.2°, 10.1±0.2°, 11.3±0.2°, 11.8±0.2°, 13.1±0.2°, 13.4±0.2°, 13.9±0.2°, 15.1±0.2°, 15.7±0.2°, 18.0±0.2°, 19.8±0.2°, 20.6±0.2°, 21.1±0.2°, 21.7±0.2°, 23.0±0.2°, 25.1±0.2°, and 27.8±0.2°.

In some embodiments, the X-ray powder diffraction characteristic diffraction angles (2θ) of Form B-II include 3.8±0.2°, 7.5±0.2°, 10.1±0.2°, 11.3±0.2°, 11.8±0.2°, 13.1±0.2°, 13.4±0.2°, 13.9±0.2°, 15.1±0.2°, 15.7±0.2°, 17.6±0.2°, 18.0±0.2°, 19.8±0.2°, 20.3±0.2°, 20.6±0.2°, 21.1±0.2°, 21.7±0.2°, 22.4±0.2°, 23.0±0.2°, 23.4±0.2°, 23.9±0.2°, 25.1±0.2°, and 27.8±0.2°.

In some embodiments, Form B-II has the X-ray powder diffraction pattern as shown in FIG. 4.

Figure 5:
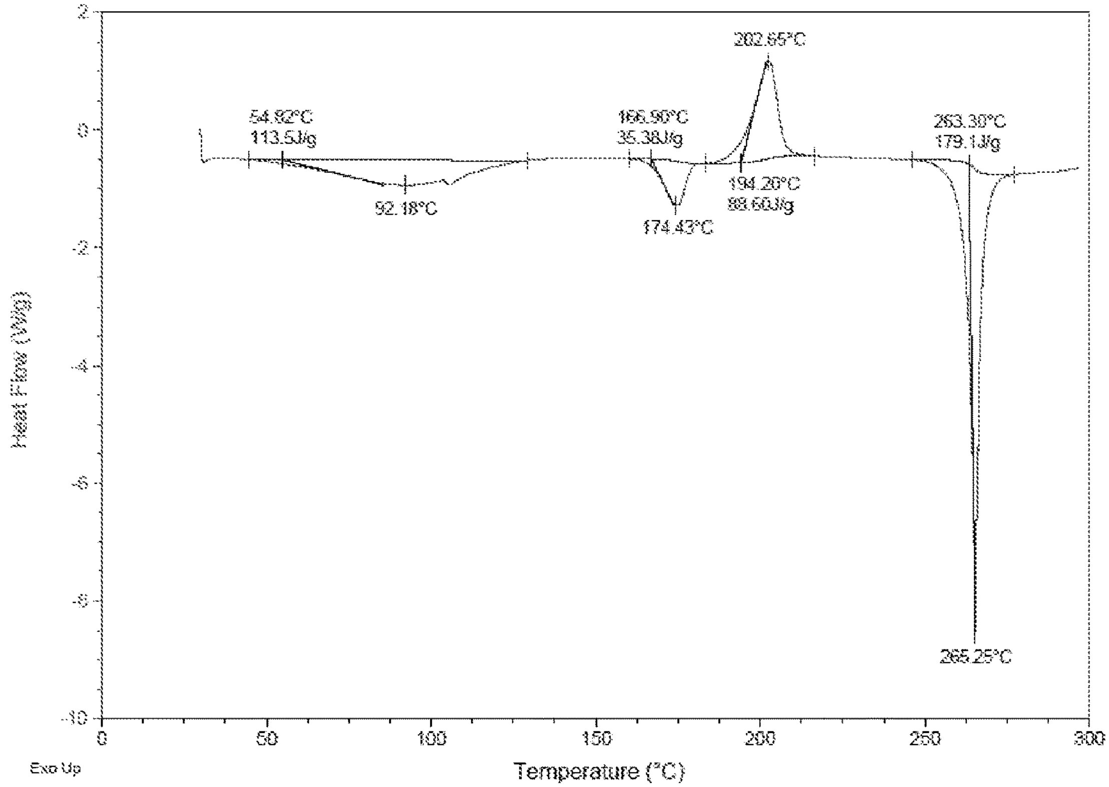
FIG. 5 shows a differential scanning calorimetry (DSC) curve of Form B-II of hemitartrate of Compound 78, wherein the horizontal axis (X-axis) plots the temperature (° C.), and the vertical axis (Y-axis) plots the heat flow (mW).

In some embodiments, Form B-II may be characterized by differential scanning calorimetry (DSC). In some embodiments, Form B-II has a DSC curve as shown in FIG. 5. In the DSC curve, Form B-II has endothermic peaks at about 54.8-92.2° C., 166.9-174.4° C., and 263.3-265.3° C., and has an exothermic peak at about 194.2-202.7° C.

In some embodiments, Form B-II may be characterized by thermogravimetric analysis (TGA). In some embodiments, Form B-II has a TGA curve as shown in FIG. 6, showing a weight loss of about 4.3% in the range from 30° C. to 100° C., which indicates that Form B-II contains much adsorbed water. From FIG. 6 in combination with the DSC curve in FIG. 5, it can be known that Form B-II is a hygroscopic metastable form.

In some embodiments, said Form B-II is substantially pure.

In some embodiments, said Form B-II is substantially free of other crystalline forms. For example, the content by weight of Form B-II is at least 99%, at least 95%, at least 90%, at least 80%, at least 70%, at least 60%, or at least 50%.

Methods for Preparing Form B-II

The present invention provides a method for preparing Form B-II, comprising:

(1) mixing the compound 4-chloro-3-(2-(2-((4-((3S,5R)-3,5-dimethylpiperazin-1-yl) phenyl)amino)pyrimidin-5-yl)ethyl)-5-methoxy-N-methylbenzamide with L-tartaric acid in ethanol under heating and stirring for reacting to form a salt;

(2) cooling the reaction obtained in step (1) to precipitate the solid sufficiently;

(3) isolating the precipitated solid as Form B-II;

(4) optionally drying the solid obtained in step (3).

In some embodiments, the molar ratio of said L-tartaric acid to the compound 4-chloro-3-(2-(2-((4-((3S,5R)-3,5-dimethylpiperazin-1-yl)phenyl)amino)pyrimidin-5-yl) ethyl)-5-methoxy-N-methylbenzamide is not less than about 1:2. In some embodiments, the molar ratio is about 4:5. In some embodiments, the molar ratio is about 3.4:1.

In some embodiments, the ratio of the volume (ml) of said ethanol to the weight (g) of the compound 4-chloro-3-(2-(2-((4-((3S,5R)-3,5-dimethylpiperazin-1-yl)phenyl)amino) pyrimidin-5-yl)ethyl)-5-methoxy-N-methylbenzamide is not less than about 10 ml/g (volume/weight ratio), such as about 72 ml/g, about 75 ml/g, and the like.

In some embodiments, in said step (1), the heating temperature should not be higher than the boiling point of the solvent system, such as 70-75° C.

In some embodiments, in said step (2), said cooling is cooling naturally or cooling at a controlled temperature, and cooling to room temperature or lower temperature, such as 20-25° C.

In some embodiments, in said step (2), after cooling, the reaction is stirred for 1-120 hours, such as 18 hours, to precipitate the solid sufficiently.

In some embodiments, in said step (4), the drying temperature and drying time can be determined conventionally by a person skilled in the art, so that the solid is dried sufficiently and the desired crystalline form is maintained. In some embodiments, the drying temperature is 50-85° C., such as 50° C., 65° C., 82° C., and the like. In some embodiments, the drying time is 1-24 hours, such as 1 hours, 18 hours, 19 hours, and the like.

Identification of Form B-III

The present invention provides Form B-III.

In some embodiments, Form B-III may be identified by X-ray powder diffraction. In some embodiments, the X-ray powder diffraction characteristic diffraction angles (2θ) of Form B-III include 13.1±0.2°, 14.6±0.2°, 18.3±0.2°, 18.9±0.2°, 19.4±0.2°, and 26.3±0.2°.

In some embodiments, the X-ray powder diffraction characteristic diffraction angles (2θ) of Form B-III include 12.4±0.2°, 13.1±0.2°, 13.7±0.2°, 14.6±0.2°, 16.5±0.2°, 18.3±0.2°, 18.9±0.2°, 19.4±0.2°, 21.4±0.2°, 22.6±0.2°, 23.7±0.2°, and 26.3±0.2°.

In some embodiments, the X-ray powder diffraction characteristic diffraction angles (2θ) of Form B-III include 7.6±0.2°, 8.9±0.2°, 10.0±0.2°, 11.0±0.2°, 12.4±0.2°, 13.1±0.2°, 13.4±0.2°, 13.7±0.2°, 14.6±0.2°, 15.9±0.2°, 16.5±0.2°, 18.3±0.2°, 18.9±0.2°, 19.4±0.2°, 21.4±0.2°, 22.6±0.2°, 23.7±0.2°, and 26.3±0.2°.

In some embodiments, the X-ray powder diffraction characteristic diffraction angles (2θ) of Form B-III include 7.6±0.2°, 8.9±0.2°, 10.0±0.2°, 11.0±0.2°, 12.4±0.2°, 13.1±0.2°, 13.4±0.2°, 13.7±0.2°, 14.6±0.2°, 15.9±0.2°, 16.5±0.2°, 17.2±0.2°, 18.3±0.2°, 18.9±0.2°, 19.4±0.2°, 19.6±0.2°, 21.4±0.2°, 22.6±0.2°, 23.7±0.2°, 24.6±0.2°, 26.3±0.2°, 27.6±0.2°, and 29.2±0.2°.

In some embodiments, the X-ray powder diffraction characteristic diffraction angles (2θ) of Form B-III include 7.6±0.2°, 8.9±0.2°, 10.0±0.2°, 11.0±0.2°, 12.4±0.2°, 13.1±0.2°, 13.4±0.2°, 13.7±0.2°, 14.6±0.2°, 15.9±0.2°, 16.5±0.2°, 17.2±0.2°, 17.9±0.2°, 18.3±0.2°, 18.9±0.2°, 19.4±0.2°, 19.6±0.2°, 20.8±0.2°, 21.4±0.2°, 22.6±0.2°, 23.2±0.2°, 23.7±0.2°, 24.6±0.2°, 26.3±0.2°, 27.1±0.2°, 27.6±0.2°, 27.8±0.2°, and 29.2±0.2°.

In some embodiments, Form B-III has the X-ray powder diffraction pattern as shown in FIG. 7.

Figure 8:
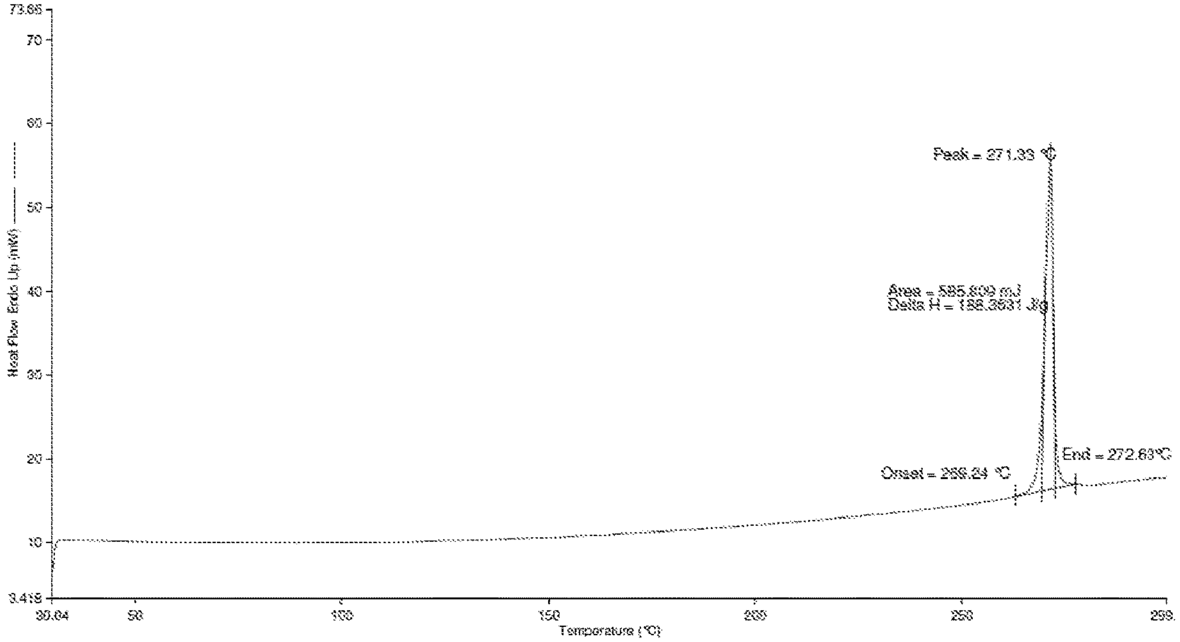
FIG. 8 shows a differential scanning calorimetry (DSC) curve of Form B-III of hemitartrate of Compound 78, wherein the horizontal axis (X-axis) plots the temperature (° C.), and the vertical axis (Y-axis) plots the heat flow (mW).

In some embodiments, Form B-III may be characterized by differential scanning calorimetry (DSC). In some embodiments, Form B-III has a DSC curve as shown in FIG. 8. In the DSC curve, the endothermic peak of Form B-III is at about 269.2-271.3° C.

In some embodiments, Form B-III may be characterized by thermogravimetric analysis (TGA).

In some embodiments, Form B-III has a TGA curve as shown in FIG. 9, indicating that Form B-III is anhydrous or neat.

In some embodiments, said Form B-III is substantially pure.

In some embodiments, said Form B-III is substantially free of other crystalline forms. For example, the content by weight of Form B-III is at least 99%, at least 95%, at least 90%, at least 80%, at least 70%, at least 60%, or at least 50%.

Methods for Preparing Form B-III

The present invention relates to a method for preparing Form B-III, comprising:

(1) mixing the compound 4-chloro-3-(2-(2-((4-((3S,5R)-3,5-dimethylpiperazin-1-yl) phenyl)amino)pyrimidin-5-yl)ethyl)-5-methoxy-N-methylbenzamide with L-tartaric acid in a dissolution solvent, in water, or in a mixed solvent consisting of water miscible organic solvent and water under heating and stirring for reacting to form a salt, thereby obtaining the first solution; provided that said dissolution solvent is not the single solvent ethanol (i.e., it may be another dissolution solvent, or may be a mixed solvent consisting of ethanol and another dissolution solvent);

(2) optionally adding an anti-dissolution solvent into said first solution to obtain the second solution;

(3) cooling said first solution or second solution to precipitate the solid sufficiently;

(4) isolating the precipitated solid as Form B-III;

(5) optionally drying the solid obtained in step (4).

In some embodiments, the molar ratio of said L-tartaric acid to the compound 4-chloro-3-(2-(2-((4-((3S,5R)-3,5-dimethylpiperazin-1-yl)phenyl)amino)pyrimidin-5-yl) ethyl)-5-methoxy-N-methylbenzamide is not less than about 1:1. In some embodiments, the molar ratio is about 1:1. In some embodiments, the molar ratio is about 1.5:1.

In some embodiments, in step (1), the ratio of the volume (ml) of said dissolution solvent, said water, or said mixed solvent consisting of water miscible organic solvent and water to the weight (g) of the compound 4-chloro-3-(2-(2-((4-((3S,5R)-3,5-dimethylpiperazin-1-yl)phenyl)amino) pyrimidin-5-yl)ethyl)-5-methoxy-N-methylbenzamide is not less than about 10 ml/g (volume/weight ratio), such as about 20 ml/g, about 30 ml/g, about 33 ml/g, about 50 ml/g, about 65 ml/g, about 98 ml/g, about 286 ml/g, and the like.

In some embodiments, said dissolution solvent is selected from $C_{1-6}$ alkanol, acetone, toluene, organic acid ester with not more than eight carbon atoms, and the mixture thereof. In some embodiments, said dissolution solvent is selected from methanol, ethanol, i-propanol, t-butanol, n-butanol, acetone, toluene, n-propyl acetate, ethyl acetate, and the mixture thereof. In some embodiments, said dissolution solvent is selected from methanol, ethanol, i-propanol, acetone, toluene, n-propyl acetate, ethyl acetate, and the mixture thereof.

In some embodiments, said dissolution solvent is selected from a mixed solvent consisting of two solvents of methanol, ethanol, toluene, n-propyl acetate, and ethyl acetate, for example, n-propyl acetate/methanol (in the volume ratio of about 3:2), toluene/ethanol (in the volume ratio of about 1:1), ethyl acetate/ethanol (in the volume ratio of about 11:15), and the like.

In some embodiments, said water miscible organic solvent is selected from $C_{1-6}$ alkanol, acetone, and the mixture thereof. In some embodiments, said water miscible organic solvent is selected from methanol, ethanol, i-propanol, t-butanol, acetone, and the mixture thereof. In some embodiments, said water miscible organic solvent is selected from ethanol, i-propanol, acetone, and the mixture thereof.

In some embodiments, the volume percentage of said water miscible organic solvent in said mixed solvent is not more than about 95%, such as 95%, 90%, 80%, and the like.

In some embodiments, said anti-dissolution solvent is selected from toluene, organic acid ester with not more than eight carbon atoms, and the mixture thereof. In some embodiments, said anti-dissolution solvent is selected from toluene, ethyl acetate, n-propyl acetate, and the mixture thereof. In some embodiments, said anti-dissolution solvent is selected from toluene, ethyl acetate, and the mixture thereof.

In some embodiments, in said step (1), the heating temperature should not be higher than the boiling point of the solvent system, such as 55-60° C., 70-72° C., 75-85° C., 90-95° C., and the like.

In some embodiments, in said step (3), said cooling is cooling naturally or cooling at a controlled temperature, and cooling to room temperature or lower temperature, such as 20-25° C., 25-30° C., and the like.

In some embodiments, in said step (3), after cooling, the first solution or the second solution is stirred for 1-120 hours, such as 2 hours, 16 hours, 17 hours, 18 hours, 20 hours, and the like, to precipitate the solid sufficiently.

In some embodiments, in said step (5), the drying temperature and drying time can be determined conventionally by a person skilled in the art, so that the solid is dried sufficiently and the desired crystalline form is maintained. In some embodiments, the drying temperature is 50-85° C., such as 55° C., 60° C., 65° C., and the like. In some embodiments, the drying time is 1-24 hours, such as 2 hours, 3 hours, 5 hours, 6 hours, 16 hours, and the like.

Identification of Form C-I

The present invention provides Form C-I.

In some embodiments, Form C-I may be identified by X-ray powder diffraction. In some embodiments, the X-ray powder diffraction characteristic diffraction angles (2θ) of Form C-I include 7.8±0.2°, 11.1±0.2°, 11.7±0.2°, 16.6±0.2°, 17.9±0.2°, 18.2±0.2°, 19.2±0.2°, and 24.0±0.2°.

In some embodiments, the X-ray powder diffraction characteristic diffraction angles (2θ) of Form C-I include 5.5±0.2°, 7.8±0.2°, 9.7±0.2°, 11.1±0.2°, 11.7±0.2°, 13.8±0.2°, 14.3±0.2°, 16.6±0.2°, 17.9±0.2°, 18.2±0.2°, 19.2±0.2°, 22.2±0.2°, 24.0±0.2°, and 26.1±0.2°.

In some embodiments, the X-ray powder diffraction characteristic diffraction angles (2θ) of Form C-I include 5.5±0.2°, 7.8±0.2°, 9.7±0.2°, 11.1±0.2°, 11.7±0.2°, 13.5±0.2°, 13.8±0.2°, 14.3±0.2°, 14.7±0.2°, 16.6±0.2°, 17.9±0.2°, 18.2±0.2°, 19.2±0.2°, 20.0±0.2°, 20.6±0.2°, 22.2±0.2°, 24.0±0.2°, 26.1±0.2°, and 27.4±0.2°.

In some embodiments, the X-ray powder diffraction characteristic diffraction angles (2θ) of Form C-I include 5.5±0.2°, 7.8±0.2°, 9.7±0.2°, 11.1±0.2°, 11.7±0.2°, 12.2±0.2°, 12.9±0.2°, 13.5±0.2°, 13.8±0.2°, 14.3±0.2°, 14.7±0.2°, 16.6±0.2°, 17.9±0.2°, 18.2±0.2°, 19.2±0.2°, 20.0±0.2°, 20.6±0.2°, 22.2±0.2°, 23.5±0.2°, 24.0±0.2°, 25.0±0.2°, 26.1±0.2°, 27.4±0.2°, and 32.8±0.2°.

In some embodiments, the X-ray powder diffraction characteristic diffraction angles (2θ) of Form C-I include 5.5±0.2°, 7.8±0.2°, 9.7±0.2°, 11.1±0.2°, 11.7±0.2°, 12.2±0.2°, 12.9±0.2°, 13.5±0.2°, 13.8±0.2°, 14.3±0.2°, 14.7±0.2°, 16.6±0.2°, 17.9±0.2°, 18.2±0.2°, 19.2±0.2°, 20.0±0.2°, 20.6±0.2°, 22.2±0.2°, 22.7±0.2°, 23.5±0.2°, 24.0±0.2°, 24.4±0.2°, 26.1±0.2°, 27.4±0.2°, 28.8±0.2°, 32.8±0.2°, and 33.6±0.2°.

In some embodiments, Form C-I has the X-ray powder diffraction pattern as shown in FIG. 12.

Figure 13:
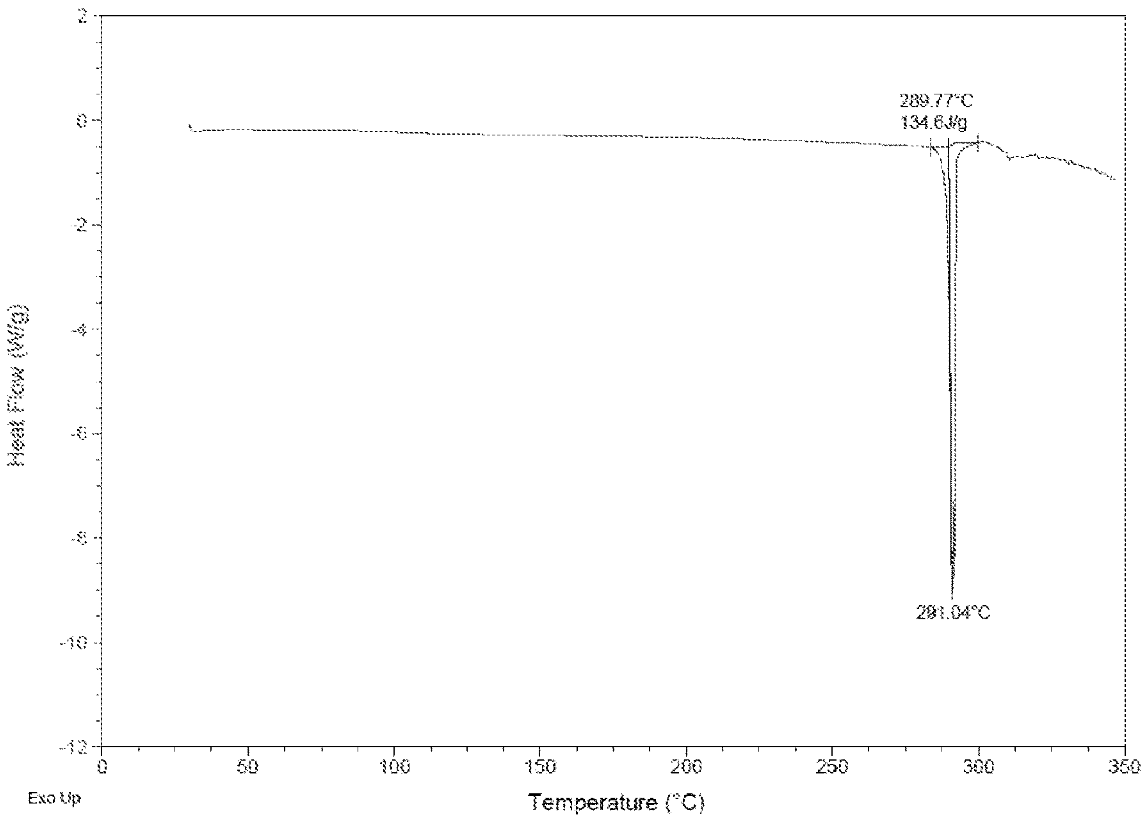
FIG. 13 shows a differential scanning calorimetry (DSC) curve of Form C-I of mono p-tosylate of Compound 78, wherein the horizontal axis (X-axis) plots the temperature (° C.), and the vertical axis (Y-axis) plots the heat flow (mW).

In some embodiments, Form C-I may be characterized by differential scanning calorimetry (DSC). In some embodiments, Form C-I has a DSC curve as shown in FIG. 13. In the DSC curve, the endothermic peak of Form C-I is at about 289.77-291.04° C.

In some embodiments, Form C-I may be characterized by thermogravimetric analysis (TGA). In some embodiments, Form C-I has a TGA curve as shown in FIG. 14, indicating that Form C-I is anhydrous or neat.

In some embodiments, said Form C-I is substantially pure.

In some embodiments, said Form C-I is substantially free of other crystalline forms. For example, the content by weight of Form C-I is at least 99%, at least 95%, at least 90%, at least 80%, at least 70%, at least 60%, or at least 50%.

Methods for Preparing Form C-I

The present invention provides a method for preparing Form C-I, comprising:

(1) mixing the compound 4-chloro-3-(2-(2-((4-((3S,5R)-3,5-dimethylpiperazin-1-yl)phenyl) amino)pyrimidin-5-yl)ethyl)-5-methoxy-N-methylbenzamide with p-toluenesulfonic acid monohydrate in a mixed solvent consisting of water miscible organic solvent and water under heating and stirring for reacting to form a salt;
(2) cooling the reaction obtained in step (1) to precipitate the solid sufficiently;
(3) isolating the precipitated solid as Form C-I;
(4) optionally drying the solid obtained in step (3).

In some embodiments, the molar ratio of said p-toluenesulfonic acid monohydrate to the compound 4-chloro-3-(2-(2-((4-((3S,5R)-3,5-dimethylpiperazin-1-yl)phenyl)amino) pyrimidin-5-yl)ethyl)-5-methoxy-N-methylbenzamide is not less than about 1:1. In some embodiments, the molar ratio is about 1.5:1.

In some embodiments, the ratio of the volume (ml) of said mixed solvent consisting of water miscible organic solvent and water to the weight (g) of the compound 4-chloro-3-(2-(2-((4-((3S,5R)-3,5-dimethylpiperazin-1-yl)phenyl)amino) pyrimidin-5-yl)ethyl)-5-methoxy-N-methylbenzamide in step (1) is not less than about 10 ml/g (volume/weight ratio), such as about 36 ml/g, about 43 ml/g, and the like.

In some embodiments, said water miscible organic solvent is selected from $C_{1-6}$ alkanol, acetone, and the mixture thereof. In some embodiments, said water miscible organic solvent is selected from i-propanol, acetone, and the mixture thereof.

In some embodiments, the volume percentage of said water miscible organic solvent in said mixed solvent is not more than about 95%, such as 80%, and the like.

In some embodiments, in said step (1), the heating temperature should not be higher than the boiling point of the solvent system, such as 55-60° C., 75-85° C., and the like.

In some embodiments, optionally, after the completion of the reaction in step (1), at least one anti-dissolution solvent (such as i-propanol) is added prior to step (2).

In some embodiments, in said step (2), said cooling is cooling naturally or cooling at a controlled temperature, and cooling to room temperature or lower temperature.

In some embodiments, in said step (2), after cooling, the reaction is stirred for 1-120 hours, such as 15 hours, and the like, to precipitate the solid sufficiently.

In some embodiments, in said optional step (4), the drying temperature and drying time can be determined conventionally by a person skilled in the art, so that the solid is dried sufficiently and the desired crystalline form is maintained. In some embodiments, the drying temperature is 50-60° C., such as 50° C., and the like. In some embodiments, the drying time is 1-24 hours, such as 4 hours, 20 hours, and the like.

The features of each embodiment specified for the methods for preparing the same crystalline form can be arbitrarily combined to produce a new embodiment. Those new embodiments obtained from such arbitrary combinations are included within the scope of the present invention, as if these embodiments obtained from such arbitrary combinations are specifically and individually listed herein.

Pharmaceutical Compositions and Uses

The salts of the present invention and the crystalline forms of the present invention are useful for inhibiting FGFR activity in vivo and in vitro.

The salts of the present invention and the crystalline forms of the present invention are useful for preventing or treating a disease responsive to inhibition of FGFR activity. Accordingly, the present invention provides a method of preventing or treating a disease responsive to inhibition of FGFR activity, comprising administering to a subject in need thereof the salts of the present invention and the crystalline forms of the present invention, and optionally administering one or more other active ingredients. Moreover, the present invention also provides use of the salts of the present invention and the crystalline forms of the present invention in the manufacture of a medicament for preventing or treating a disease responsive to inhibition of FGFR activity. Said disease responsive to inhibition of FGFR activity is such as cancer, said cancer includes, but not limited to, lung cancer (such as squamous non-small cell lung cancer and small cell lung cancer), gastric cancer, liver cancer, breast cancer, ovarian cancer, endometrial cancer, bladder cancer, urothelial cancer, esophageal cancer, biliary tract cancer, colon cancer, rectal cancer, head and neck cancer, cervical cancer, pancreatic cancer, adrenal cancer, glioma, mesothelioma, and hematologic malignancy (such as myeloproliferative neoplasm).

The salts of the present invention and the crystalline forms of the present invention can be administered in any suitable manners, including oral, topical (including buccal and sublingual), rectal, vaginal, transdermal, intramuscular, intravenous, intraarterial, intraperitoneal, intrapulmonary, intradermal, subcutaneous, intrathecal, epidural and intranasal administration.

The dosing amount of the salts of the present invention and the crystalline forms of the present invention to achieve the desired physiological effect may depend on a number of factors, e.g., the disease to be treated, the route and mode of administration, and the clinical condition of the patient. The daily dosage may, for example, range from 0.01 mg/day to 3 g/day, such as from 0.05 mg/day to 2 g/day, or from 100 mg/day to 1 g/day. Said daily dosage may be administered in one dose or in several divided doses (such as in 2-4 divided doses).

For the preventing or treating of the above-mentioned diseases, the salts of the present invention and the crystalline forms of the present invention may be administered as such, but typically in a pharmaceutical composition formulated with a pharmaceutically acceptable carrier.

The pharmaceutical composition of the present invention can be any forms that are convenient for administration, such as tablet, powder, capsule, solution, dispersion, suspension, syrup, spray, suppository, gel, emulsion, and patch. The pharmaceutically acceptable carrier used for the preparation of pharmaceutical composition may be conventional components in the field of pharmaceutical formulation, such as diluent, disintegrating agent, lubricant, pH regulator, flavoring agent, filler, preservative, osmotic pressure regulator, colorant, emulsifier, suspending agent, and surfactant. Said pharmaceutically acceptable carrier should be compatible with the other ingredients of the pharmaceutical composition and does not have harmful effect on the subject's health. The carrier may be a solid or a liquid or both. The pharmaceutical composition may contain from 0.05% to 95% by weight of the salts of the present invention and the crystalline forms of the present invention.

Said pharmaceutical composition can be produced by mixing the salts of the present invention or the crystalline forms of the present invention with a pharmaceutically acceptable carrier. Carriers suitable for each dosage form are well known to those skilled in the art, for example, are described in detail in the following literatures: Ansel, Howard C. et al, *Ansel's Pharmaceutical Dosage Forms and Drug Delivery Systems*. Philadelphia: Lippincott, Williams & Wilkins, 2004; Gennaro, Alfonso R. et al *Remington: The Science and Practice of Pharmacy*. Philadelphia: Lippincott, Williams & Wilkins, 2000; and Rowe, R. C. *Handbook of Pharmaceutical Excipients*. Chicago, Pharmaceutical Press, 2005.

In some examples, the crystalline forms of the present invention will not be converted to other forms when being formulated with one or more pharmaceutically acceptable carriers. In other examples, the crystalline forms of the present invention may be converted completely or partially to one or more other forms, when being formulated with one or more pharmaceutically acceptable carriers. However, those skilled in the art can use known technical means to maintain the stability of the crystalline form as required. In some examples, the crystalline forms of the present invention can be dissolved when being formulated into a pharmaceutical composition, thus no longer exists in their respective crystalline forms in the pharmaceutical composition.

The salts of the present invention and the crystalline forms of the present invention can be administered in combination with one or more other active ingredients, to achieve additive or synergetic therapeutic effect, or to reduce side effects. When administered in combination, the salts of the present invention and the crystalline forms of the present invention and said one or more other active ingredients can be formulated in separate dosage forms for administration at the same time or sequentially through the same or different administration routes, or can be administered at the same time in the same unit dosage form.

The other active ingredients that can be administered in combination with the salts of the present invention and the crystalline forms of the present invention may be anti-neoplastic agents and/or anti-neoplastic therapy. Examples include but not limited to: radiotherapy, immunotherapeutic agents, chemotherapeutic agents such as DNA-damaging chemotherapeutic agents and cell replication-interfering chemotherapeutic agents.

Non-limiting examples of DNA-damaging chemotherapeutic agents include topoisomerase I inhibitors (e.g., irinotecan, topotecan, camptothecin and analogs or metabolites thereof, and adriamycin); topoisomerase II inhibitors (e.g., etoposide, teniposide, mitoxantrone, idarubicin, and daunorubicin); alkylating agents (e.g., melphalan, chlorambucil, busulfan, thiotepa, ifosfamide, carmustine, lomustine, semustine, streptozocin, dacarbazine, methotrexate, mitomycin C, and cyclophosphamide); DNA intercalators (e.g., cisplatin, oxaliplatin, and carboplatin); DNA intercalators and free radical generators such as bleomycin; and nucleoside analogs (e.g., 5-fluorouracil, capecitabine, gemcitabine, fludarabine, cytarabine, azacitidine, mercaptopurine, thioguanine, pentostatin, and hydroxyurea).

Non-limiting examples of cell replication-interfering chemotherapeutic agents include: paclitaxel, docetaxel, and related analogs; vincristine, vinblastin, and related analogs; thalidomide and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinase; antibodies which bind to proteins overexpressed in cancers and thereby down-regulate cell replication (e.g., trastuzumab, rituximab, cetuximab, and bevacizumab); and inhibitors of other proteins or enzymes known to be upregulated, over-expressed, or activated in cancers, the inhibition of which can down-regulate cell replication.

EXAMPLES

The following examples are used to illustrate the present invention without limiting the scope defined in the claims.

Experiments

Figure 22:
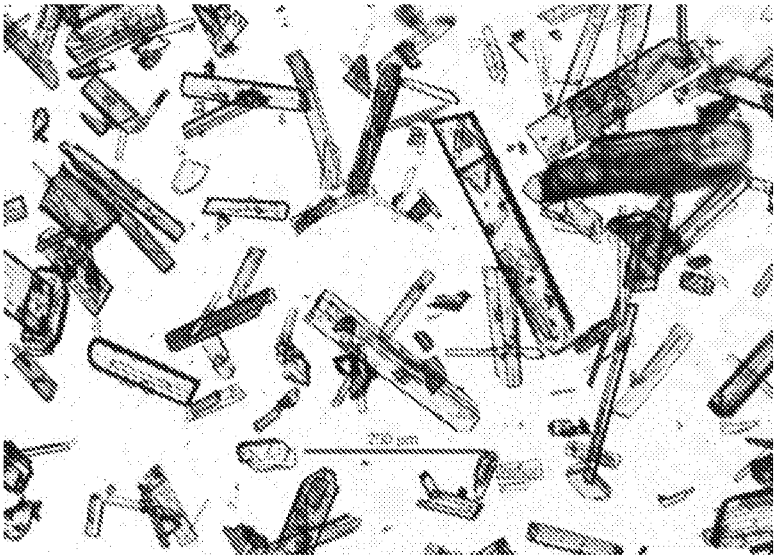
FIG. 22 shows a microphotograph of Compound 78 in free form prepared according to Example 9 of WO2014/139465A1, showing that it is an acicular crystal.

The compound 4-chloro-3-(2-(2-((4-((3S,5R)-3,5-dimethylpiperazin-1-yl)phenyl)amino) pyrimidin-5-yl)ethyl)-5-methoxy-N-methylbenzamide raw material used in the examples was prepared according to the method of Example 9 of WO2014/139465A1, which is a yellow acicular crystal, and has a microphotograph as shown in FIG. 22.

All reagents, except intermediates, used in this disclosure are commercially available. The names of all compounds, except the reagents, were generated by ChemDraw Professional 16.0.

Unless otherwise indicated, X-ray powder diffraction patterns were obtained using Germany Bruker D8 ADVANCE X-ray diffractometer (target: Cu; voltage: 40 kV; current: 40 mA; scanning speed: 4 degrees/min; step size: 0.02 degree; scanning range: 3-45 degrees).

Unless otherwise indicated, differential scanning calorimetry (DSC) was performed on Germany NETZSCH DSC 204F1 (purge gas: nitrogen; flow rate: 20-60 mL $min^{-1}$; heating rate: 10° C./min; temperature range: 30° C. to 300/350° C.). The samples were measured in the pricked aluminum pans. Indium was used for temperature calibration.

Unless otherwise indicated, thermogravimetry (TG) analyses were performed using Germany NETZSCH TGA 209F1 (purge gas: nitrogen; heating rate: 10° C./min).

Unless otherwise indicated, the microphotographs were obtained using Nikon Ci-L microscope.

Example 1—Preparation of Form A-III 4-chloro-3-(2-(2-((4-((3S,5R)-3,5-dimethylpiperazin-1-yl)phenyl)amino)pyrimidin-5-yl)ethyl)-5-methoxy-N-methylbenzamide (0.51 g, 1 mmol) was suspended in 10 ml of 95% ethanol (i.e., a mixture of ethanol:water in the volume ratio of 95:5), and heated to 75-85° C. under stirring. 100 μL of hydrochloric acid (with the concentration of 36%-38% by weight) was added to the suspension to give a clear solution. The solution was cooled to 15-25° C., and stirred for 20 hours.

The solid was filtered out and dried at 60° C. under vacuum for 2 hours to give the sample. The content of chloride ion in the sample was determined as 6.48%, from which it was judged that the obtained sample was monohydrochloride (theoretical content: 6.69%)

$^1H$ NMR (400 MHz, CD3OD) δ 8.11 (2H, s), 7.48-7.42 (2H, m), 7.36 (1H, d, J=2.0), 7.29 (1H, d, J=2.0), 7.00 (2H, dd, J=9.6, 2.8), 3.91 (3H, s), 3.73 (2H, dd, J=13.3, 2.4), 3.48 (2H, ddd, J=9.9, 6.6, 3.2), 3.05 (2H, t, J=7.5), 2.89 (3H, s), 2.82 (2H, t, J=7.5), 2.69 (2H, dd, J=13.3, 11.3), 1.38 (6H, d, J=6.6).

The obtained powder sample was Form A-III, which had the X-ray powder diffraction pattern as shown in FIG. 1, including diffraction peaks (2θ): 5.8±0.2°, 6.2±0.2°, 7.9±0.2°, 10.3±0.2°, 12.3±0.2°, 13.3±0.2°, 15.0±0.2°, 15.8±0.2°, 16.2±0.2°, 16.8±0.2°, 17.4±0.2°, 18.3±0.2°, 18.5±0.2°, 19.6±0.2°, 20.2±0.2°, 21.0±0.2°, 21.4±0.2°, 22.2±0.2°, 23.1±0.2°, 24.1±0.2°, 24.8±0.2°, 25.2±0.2°, 26.0±0.2°, 26.4±0.2°, 27.1±0.2°, 27.8±0.2°, 29.8±0.2°, 31.5±0.2°, and 32.7±0.2°, wherein characteristic peaks (2θ) are at 5.8±0.2°, 6.2±0.2°, 10.3±0.2°, 12.3±0.2°, 13.3±0.2°, 15.0±0.2°, 16.2±0.2°, 22.2±0.2°, 23.1±0.2°, 24.1±0.2°, and 26.4±0.2°. DSC result of the sample was as shown in FIG. 2, indicating that the endothermic peak of Form A-III was at about 290.2-295.4° C.

Example 2—Preparation of Form A-III 4-chloro-3-(2-(2-((4-((3S,5R)-3,5-dimethylpiperazin-1-yl)phenyl)amino)pyrimidin-5-yl)ethyl)-5-methoxy-N-methylbenzamide (0.51 g, 1 mmol) was suspended in 30 ml of anhydrous ethanol, and heated to 75-85° C. under stirring to dissolve. 100 μL of hydrochloric acid (with the concentration of 36%-38% by weight) was added to the solution, and the stirring was continued at 75-85° C. for 5 minutes. The solution was cooled to 15-25° C., and stirred for 2 hours. The solid was filtered out and dried at 60° C. under vacuum for 18 hours to give the sample. Upon measurement, the X-ray powder diffraction pattern of the obtained sample was consistent with that of Form A-III sample obtained in Example 1.

Example 3—Preparation of Form A-III 4-chloro-3-(2-(2-((4-((3S,5R)-3,5-dimethylpiperazin-1-yl)phenyl)amino)pyrimidin-5-yl)ethyl)-5-methoxy-N-methylbenzamide (2.04 g, 4 mmol) was suspended in 40 ml of a mixture of i-propanol:water having the volume ratio of 9:1, and heated to 75-80° C. under stirring. 352 μL of hydrochloric acid (with the concentration of 36%-38% by weight) was added to the suspension. The resulting mixture was cooled to 20-25° C., and stirred for 2 hours. The solid was filtered out and dried at 60° C. under vacuum for 2 hours to give 1.6 g sample. Upon measurement, the X-ray powder diffraction pattern of the obtained sample was consistent with that of Form A-III sample obtained in Example 1.

Example 4—Preparation of Form B-II 4-chloro-3-(2-(2-((4-((3S,5R)-3,5-dimethylpiperazin-1-yl)phenyl)amino)pyrimidin-5-yl)ethyl)-5-methoxy-N-methylbenzamide (1 g, 1.96 mmol) and 60 ml of anhydrous ethanol were mixed, and heated to 70-74° C. to dissolve. A solution of L-tartaric acid (0.24 g, 1.6 mmol) in ethanol (12 ml) was added, and the solid precipitated immediately. The mixture was stirred at 70-74° C. for 30 minutes; cooled to 50-55° C., and stirred for 1 hour; cooled to 20-25° C., and stirred for 18 hours. The solid was filtered out and dried at 60° C. under vacuum for 2 hours, then dried at 65° C. under vacuum for 16 hours, and then dried at 82° C. under vacuum for 1 hour, to give 1.15 g sample.

$^1$H NMR (400 MHz, DMSO) δ 9.22 (1H, s), 8.48 (1H, q, J=4.4), 8.22 (2H, s), 7.53 (2H, dd, J=9.7, 2.7), 7.43 (1H, d, J=1.9), 7.40 (1H, d, J=1.9), 6.88 (2H, dd, J=9.7, 2.7), 3.88 (3H, s), 3.83 (1H, s), 3.53 (2H, d, J=9.8), 3.09 (2H, d, J=6.6), 2.97 (2H, dd, J=9.1, 6.5), 2.80-2.70 (5H, m, J=14.4, 5.7), 2.30 (2H, t, J=11.4), 1.12 (6H, d, J=6.4).

The obtained powder sample was Form B-II, which had the X-ray powder diffraction pattern as shown in FIG. 4, including diffraction peaks (2θ): 3.8±0.2°, 7.5±0.2°, 10.1±0.2°, 11.3±0.2°, 11.8±0.2°, 13.1±0.2°, 13.4±0.2°, 13.9±0.2°, 15.1±0.2°, 15.7±0.2°, 17.6±0.2°, 18.0±0.2°, 19.8±0.2°, 20.3±0.2°, 20.6±0.2°, 21.1±0.2°, 21.7±0.2°, 22.4±0.2°, 23.0±0.2°, 23.4±0.2°, 23.9±0.2°, 25.1±0.2°, and 27.8±0.2°, wherein characteristic peaks (2θ) are at 7.5±0.2°, 11.3±0.2°, 13.9±0.2°, 15.1±0.2°, 18.0±0.2°, and 20.6±0.2°. The DSC result of the sample was as shown in FIG. 5, indicating that Form B-II had endothermic peaks at about 54.8-92.2° C., 166.9-174.4° C., and 263.3-265.3° C., and an exothermic peak at about 194.2-202.7° C.

Example 5—Preparation of Form B-II 4-chloro-3-(2-(2-((4-((3S,5R)-3,5-dimethylpiperazin-1-yl)phenyl)amino)pyrimidin-5-yl)ethyl)-5-methoxy-N-methylbenzamide (1 g, 1.96 mmol) and 60 ml of anhydrous ethanol were mixed, heated to 70-75° C., and filtered while hot to remove a small amount of insoluble substances. A solution of L-tartaric acid (1 g, 6.66 mmol) in ethanol (15 ml) was added. During the addition, solid precipitated. The mixture was stirred at 70-75° C. for 1 hour, and cooled to 24° C. The solid was filtered out and dried at 50° C. under vacuum for 17 hours, then dried at 82° C. under vacuum for 1 hour, to give the sample. Upon measurement, the X-ray powder diffraction pattern of the obtained sample was consistent with that of Form B-II sample obtained in Example 4.

Example 6—Preparation of Form B-III 4-chloro-3-(2-(2-((4-((3S,5R)-3,5-dimethylpiperazin-1-yl)phenyl)amino)pyrimidin-5-yl)ethyl)-5-methoxy-N-methylbenzamide (1 g, 1.96 mmol) and 15 ml of a mixture of i-propanol:water having the volume ratio of 8:2 were mixed, and heated to 70° C. to dissolve. A solution of L-tartaric acid (0.29 g, 1.93 mmol) in a mixture of i-propanol:water having the volume ratio of 8:2 (5 ml) was added to give a clear reaction solution. The solution was stirred at 70-72° C. for 10 minutes, and solid precipitated. Then the mixture was kept warm for 30 minutes, cooled to 50-55° C. and stirred for 1 hour, then cooled to 40-45° C. and stirred for 1 hour, and cooled to 20-25° C. and stirred for 17 hours. Then the solid was filtered out and dried at 60° C. under vacuum for 30 minutes, then dried at 65° C. under vacuum for 16 hours, to give 0.97 g sample.

$^1$H NMR (400 MHz, DMSO) δ 9.22 (1H, s), 8.48 (1H, q, J=4.3), 8.22 (2H, s), 7.55-7.50 (2H, m), 7.43 (1H, d, J=1.9), 7.40 (1H, d, J=1.9), 6.88 (2H, dd, J=9.7, 2.7), 3.88 (3H, s), 3.84 (1H, s), 3.57-3.48 (2H, m), 3.09 (2H, dd, J=11.6, 4.9), 2.97 (2H, dd, J=9.1, 6.5), 2.82-2.69 (5H, m, J=14.6, 5.8), 2.30 (2H, t, J=11.4), 1.13 (6H, d, J=6.4).

The obtained powder sample was Form B-III, which had the X-ray powder diffraction pattern as shown in FIG. 7, including diffraction peaks (2θ): 7.6±0.2°, 8.9±0.2°, 10.0±0.2°, 11.0±0.2°, 12.4±0.2°, 13.1±0.2°, 13.4±0.2°, 13.7±0.2°, 14.6±0.2°, 15.9±0.2°, 16.5±0.2°, 17.2±0.2°, 17.9±0.2°, 18.3±0.2°, 18.9±0.2°, 19.4±0.2°, 19.6±0.2°, 20.8±0.2°, 21.4±0.2°, 22.6±0.2°, 23.2±0.2°, 23.7±0.2°, 24.6±0.2°, 26.3±0.2°, 27.1±0.2°, 27.6±0.2°, 27.8±0.2°, and 29.2±0.2°, wherein characteristic peaks (2θ) are at 13.1±0.2°, 14.6±0.2°, 18.3±0.2°, 18.9±0.2°, 19.4±0.2°, and 26.3±0.2°. DSC result of the sample was as shown in FIG. 8, indicating that the endothermic peak of Form B-III was at about 269.2-271.3° C.

Figure 23:
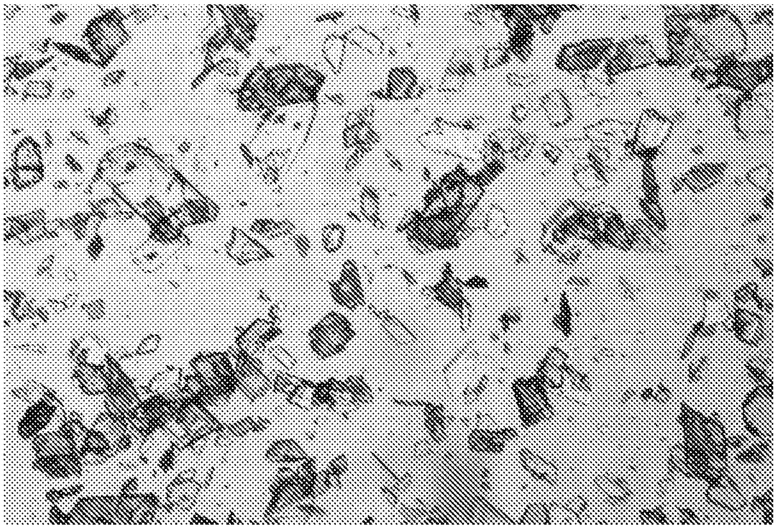
FIG. 23 shows a microphotograph of Form B-III of hemitartrate of Compound 78, showing that it is a tabular crystal.

The microscopic examination showed that Form B-III was a tabular crystal, and had the microphotograph as shown in FIG. 23.

Example 7—Preparation of Form B-III 4-chloro-3-(2-(2-((4-((3S,5R)-3,5-dimethylpiperazin-1-yl)phenyl)amino)pyrimidin-5-yl)ethyl)-5-methoxy-N-methylbenzamide (0.26 g, 0.51 mmol) was dissolved in 7 ml of a mixture of acetone:water having the volume ratio of 8:2 under reflux and stirring. A solution of L-tartaric acid (0.08 g, 0.53 mmol) in a mixture of acetone:water having the volume ratio of 8:2 (1.5 ml) was added. The mixture was cooled to 40° C. and stirred for 1 hour; cooled to 25° C. and stirred for 2 hours. The precipitated solid was filtered out and dried at 55° C. under vacuum for 2 hours to give 0.21 g sample. Upon measurement, the X-ray powder diffraction pattern of the obtained sample was consistent with that of Form B-III sample obtained in Example 6.

Example 8—Preparation of Form B-III 4-chloro-3-(2-(2-((4-((3S,5R)-3,5-dimethylpiperazin-1-yl)phenyl)amino)pyrimidin-5-yl)ethyl)-5-methoxy-N-methylbenzamide (51 mg, 0.1 mmol) was dissolved in 1.5 ml of methanol at 55-60° C., and filtered while hot. L-tartaric acid (23 mg, 0.15 mmol) was added to the filtrate, and stirring was continued at 55-60° C. for 30 minutes. Then the reaction system was cooled to 20-25° C. and stirred for 18 hours. The precipitated solid was filtered out and dried at 55° C. under vacuum for 5 hours to give the sample. Upon measurement, the X-ray powder diffraction pattern of the obtained sample was consistent with that of Form B-III sample obtained in Example 6.

Example 9—Preparation of Form B-III 4-chloro-3-(2-(2-((4-((3S,5R)-3,5-dimethylpiperazin-1-yl)phenyl)amino)pyrimidin-5-yl)ethyl)-5-methoxy-N-methylbenzamide (51 mg, 0.1 mmol) was dissolved in 3 ml of n-propyl acetate at 75-85° C. A solution of L-tartaric acid (23 mg, 0.1 mmol) in methanol (1 ml) was added, and then 1 ml of additional methanol was added. The mixture was stirred at 75-85° C. for 50 minutes; cooled to 25-30° C. and stirred for 16 hours. The precipitated solid was filtered out and dried at 55° C. under vacuum for 6 hours to give the sample. Upon measurement, the X-ray powder diffraction pattern of the obtained sample was consistent with that of Form B-III sample obtained in Example 6.

Example 10—Preparation of Form B-III 4-chloro-3-(2-(2-((4-((3S,5R)-3,5-dimethylpiperazin-1-yl)phenyl)amino)pyrimidin-5-yl)ethyl)-5-methoxy-N-methylbenzamide (21 mg, 0.041 mmol) was dissolved in 3 ml of toluene at 90-95° C. A solution of L-tartaric acid (9.3 mg, 0.062 mmol) in ethanol (0.5 ml) was added; then 2.5 ml of additional ethanol was added. The mixture was stirred at 80-90° C. for 30 minutes; cooled to 20-25° C. and stirred for 18 hours. The precipitated solid was filtered out and dried at 55° C. under vacuum for 2 hours to give the sample. Upon measurement, the X-ray powder diffraction pattern of the obtained sample was consistent with that of Form B-III sample obtained in Example 6.

Example 11—Preparation of Form B-III 4-chloro-3-(2-(2-((4-((3S,5R)-3,5-dimethylpiperazin-1-yl)phenyl)amino)pyrimidin-5-yl)ethyl)-5-methoxy-N-methylbenzamide (0.26 g, 0.51 mmol) was dissolved in 6 ml of a mixture of ethanol:water having the volume ratio of 9:1 under reflux. A solution of L-tartaric acid (0.08 g, 0.53 mmol) in a mixture of ethanol:water having the volume ratio of 9:1 (1.5 ml) was added, and the solid precipitated after 5 minutes. The heating was stopped, and the mixture was cooled to 25-30° C. and stirred for 20 hours. The precipitated solid was filtered out and dried at 55° C. under vacuum for 3 hours to give 0.27 g sample. Upon measurement, the X-ray powder diffraction pattern of the obtained sample was consistent with that of Form B-III sample obtained in Example 6.

Example 12—Preparation of Form B-III 4-chloro-3-(2-(2-((4-((3S,5R)-3,5-dimethylpiperazin-1-yl)phenyl)amino)pyrimidin-5-yl)ethyl)-5-methoxy-N-methylbenzamide (0.26 g, 0.51 mmol) was dissolved in 11 ml of a mixed solvent (ethanol/ethyl acetate in the volume ratio of 1:1) at 75-80° C. A solution of L-tartaric acid (0.08 g, 0.53 mmol) in ethanol (2 ml) was added, and the solid precipitated within 2 minutes. The mixture was stirred at 75-80° C. for 1 hour. The heating was stopped, and the mixture was cooled to 25-30° C. and stirred for 16 hours. The precipitated solid was filtered out and dried at 55° C. under vacuum for 16 hours to give 0.30 g sample. Upon measurement, the X-ray powder diffraction pattern of the obtained sample was consistent with that of Form B-III sample obtained in Example 6.

Example 13—Preparation of Form B-III 4-chloro-3-(2-(2-((4-((3S,5R)-3,5-dimethylpiperazin-1-yl)phenyl)amino)pyrimidin-5-yl)ethyl)-5-methoxy-N-methylbenzamide (0.26 g, 0.51 mmol) was dissolved in 6 ml of a mixture of i-propanol:water having the volume ratio of 9:1 under reflux. A solution of L-tartaric acid (0.08 g, 0.53 mmol) in a mixture of i-propanol:water having the volume ratio of 9:1 (2 ml) was added. The mixture was cooled to 25-30° C. and stirred for 17 hours. The solid was filtered out and dried at 55° C. under vacuum for 6 hours to give 0.24 g sample. Upon measurement, the X-ray powder diffraction pattern of the obtained sample was consistent with that of Form B-III sample obtained in Example 6.

Example 14—Preparation of Form B-III 4-chloro-3-(2-(2-((4-((3S,5R)-3,5-dimethylpiperazin-1-yl)phenyl)amino)pyrimidin-5-yl)ethyl)-5-methoxy-N-methylbenzamide (0.26 g, 0.51 mmol) was suspended in 15 ml of water, and did not dissolve when the mixture was heated to 75-85° C. A solution of L-tartaric acid (0.08 g, 0.53 mmol) in water (2 ml) was added to the suspension to give a clear solution, after which solid precipitated. The mixture was stirred at 75-85° C. for 2 hours; cooled to 25-30° C. and stirred for 19-20 hours. The precipitated solid was filtered out and dried at 55° C. under vacuum for 3 hours to give 0.23 g sample. Upon measurement, the X-ray powder diffraction pattern of the obtained sample was consistent with that of Form B-III sample obtained in Example 6.

Example 15—Preparation of Form C-I 4-chloro-3-(2-(2-((4-((3S,5R)-3,5-dimethylpiperazin-1-yl)phenyl)amino)pyrimidin-5-yl)ethyl)-5-methoxy-N-methylbenzamide (300 mg, 0.59 mmol) was dissolved in 12 ml of a mixture of acetone:water having the volume ratio of 8:2 under reflux. A solution of p-toluenesulfonic acid monohydrate (168 mg, 0.89 mmol) in a mixture of acetone:water having the volume ratio of 8:2 (1 ml) was added. After about 5 minutes under stirring, solid precipitated. The reaction was cooled to room temperature and stirring was continued for about 15 hours. The solid was filtered out and dried at 50° C. under vacuum for 4 hours to give the sample.

$^1$H NMR (400 MHz, DMSO) δ: 9.29 (s, 1H), 8.90 (d, J=9.7 Hz, 1H), 8.49 (q, J=4.3 Hz, 1H), 8.34-8.24 (m, 1H), 8.23 (s, 2H), 7.57 (t, J=6.1 Hz, 2H), 7.46 (d, J=8.0 Hz, 2H), 7.41 (dd, J=13.0, 1.8 Hz, 2H), 7.09 (dd, J=7.9, 0.5 Hz, 2H), 6.91 (d, J=9.1 Hz, 2H), 3.87 (s, 3H), 3.69 (d, J=10.9 Hz, 2H), 3.38 (d, J=6.5 Hz, 2H), 3.00-2.92 (m, 2H), 2.74 (dd, J=11.5, 5.8 Hz, 5H), 2.51 (dd, J=19.2, 7.7 Hz, 2H), 2.26 (s, 3H), 1.23 (d, J=6.5 Hz, 6H).

The obtained powder sample was Form C-I, which had the X-ray powder diffraction pattern as shown in FIG. 12, including diffraction peaks (2θ): 5.5±0.2°, 7.8±0.2°, 9.7±0.2°, 11.1±0.2°, 11.7±0.2°, 12.2±0.2°, 12.9±0.2°, 13.5±0.2°, 13.8±0.2°, 14.3±0.2°, 14.7±0.2°, 16.6±0.2°, 17.9±0.2°, 18.2±0.2°, 19.2±0.2°, 20.0±0.2°, 20.6±0.2°, 22.2±0.2°, 22.7±0.2°, 23.5±0.2°, 24.0±0.2°, 24.4±0.2°, 26.1±0.2°, 27.4±0.2°, 28.8±0.2°, 32.8±0.2°, and 33.6±0.2°. DSC result of the sample was as shown in FIG. 13, indicating that the endothermic peak of Form C-I was at about 289.77-291.04° C.

Example 16—Preparation of Form C-I 4-chloro-3-(2-(2-((4-((3S,5R)-3,5-dimethylpiperazin-1-yl)phenyl)amino)pyrimidin-5-yl)ethyl)-5-methoxy-N-methylbenzamide (4.3 g, 8.44 mmol) was dissolved in 155 ml of a mixture of i-propanol:water having the volume ratio of 8:2 under reflux, and filtered while hot to remove the insoluble substances. The filtrate was heated to reflux again, to which a solution of p-toluenesulfonic acid monohydrate (2.4 g, 12.67 mmol) in water (2 ml) was added, then 50 ml of i-propanol was added. After about 5 minutes under stirring, solid precipitated. The reaction was cooled to room temperature, and stirring was continued for about 15 hours. The solid was filtered out and dried at 50° C. under vacuum for 20 hours to give the sample. Upon measurement, the X-ray powder diffraction pattern of the obtained sample was consistent with that of Form C-I sample obtained in Example 15.

Example 17—Stability of the Salts of the Present Invention Under High Temperature, High Humidity and Illumination Determination method: the test samples of Form B-III of hemitartrate of Compound 78 and Form A-III of monohydrochloride of Compound 78 were placed on culture dishes respectively, which were subsequently placed uncovered in sealed clean containers. The containers were placed at a temperature of 60° C., at a temperature of 25° C. and a relative humidity of 92.5%5%, and under an illumination of 45001x±5001x for 10 days, respectively. Then the test samples were collected respectively to determine the purity and crystalline form of the samples. The results were shown in Table 1.

TABLE 1

Results of stability tests of Form B-III and Form A-III

| | | | Test condition | | | | | |
|---|---|---|---|---|---|---|---|---|
| | | | High temperature (60° C.) | | High humidity (92.5% RH) | | Illumination (4500 Lx) | |
| Sample placing time | | 0 day | 5 days | 10 days | 5 days | 10 days | 5 days | 10 days |
| Hemitartrate | Form | B-III | B-III | B-III | B-III | B-III | B-III | B-III |
| Form B-III | Chemical purity (%) | 98.69 | 98.72 | 98.73 | 98.78 | 98.76 | 98.76 | 98.78 |
| Monohydrochloride | Form | A-III | A-III | A-III | Changed | Changed | A-III | A-III |
| Form A-III | Chemical purity (%) | 99.57 | 99.61 | 99.56 | 99.58 | 99.61 | 99.59 | 99.60 |

Figure 15:
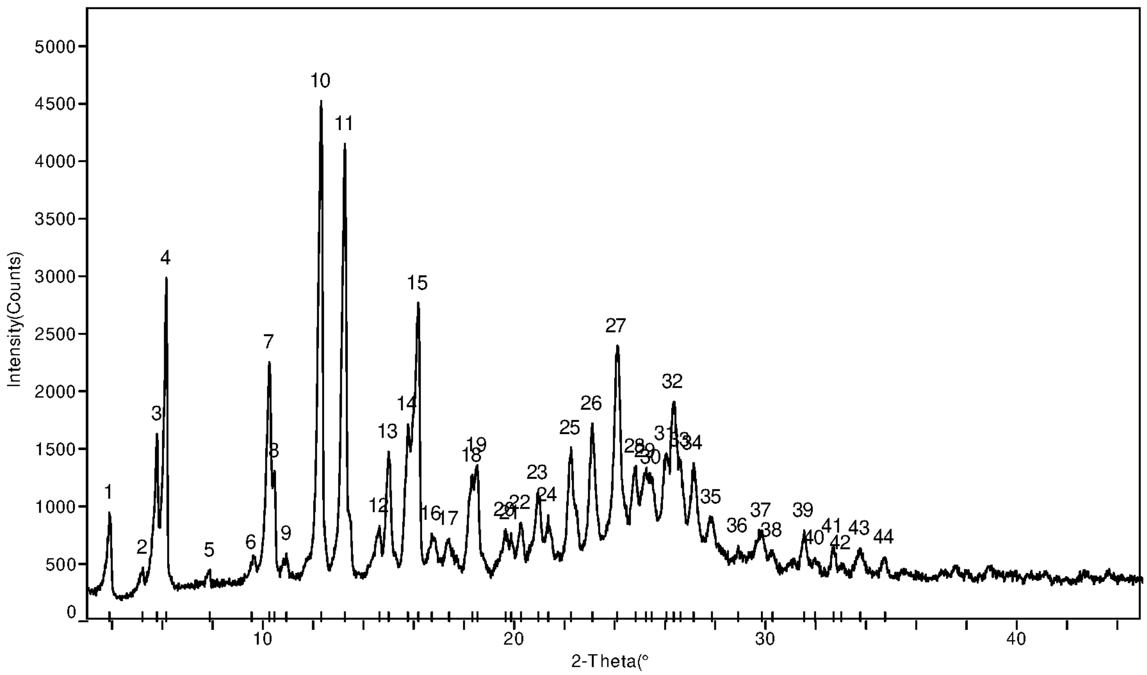
FIG. 15 shows an X-ray powder diffraction pattern of Form A-III of monohydrochloride of Compound 78 after being placed under the condition of high humidity (25° C., the relative humidity of 92.5%±5%) for 5 days, wherein the horizontal axis (X-axis) plots the diffraction angle 2 theta, and the vertical axis (Y-axis) plots the diffraction intensity.
Figure 16:
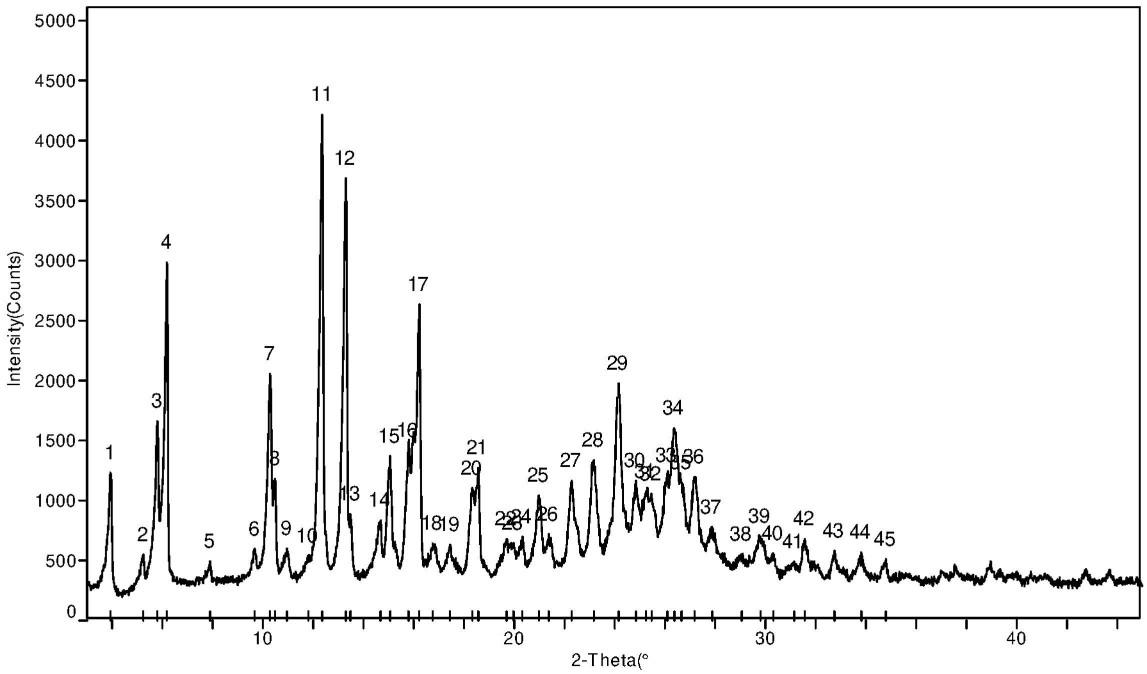
FIG. 16 shows an X-ray powder diffraction pattern of Form A-III of monohydrochloride of Compound 78 after being placed under the condition of high humidity (25° C., the relative humidity of 92.5%±5%) for 10 days, wherein the horizontal axis (X-axis) plots the diffraction angle 2 theta, and the vertical axis (Y-axis) plots the diffraction intensity.

The data in Table 1 showed that the chemical purity of Form B-III of hemitartrate of Compound 78 and Form A-III of monohydrochloride of Compound 78 was not changed significantly after being placed under high temperature, high humidity, or illumination for 10 days; the crystalline form of Form A-III sample changed after being placed under high humidity condition (as shown in FIGS. 15 and 16), but kept unchanged under high temperature and illumination conditions; while Form B-III did not change significantly under all test conditions and had a better stability.

Example 18—Stability of Form B-II and Form B-III

Determination method 1: the test samples of Form B-II and Form B-III of hemitartrate of Compound 78 were placed on culture dishes respectively, which were subsequently placed uncovered in sealed clean containers. The containers were placed at a temperature of 25° C. and a relative humidity of 92.5%5% for 3 days or 5 days. Then the crystalline form of the test samples was determined. The results were shown in Table 2.

Determination method 2: the test samples of Form B-II and Form B-III of hemitartrate of Compound 78 were suspended in water and stirred at room temperature. The test samples were collected on the second day and the fourth day for determination of crystalline form respectively. The results were shown in Table 2.

TABLE 2

| Results of stability tests of Form B-II and Form B-III of hemitartrate of Compound 78 | | | |
|---|---|---|---|
| Test condition | High humidity (92.5% RH) | Slurried in water | |
| Sampling time | 3 days or 5 days | 2 days | 4 days |
| Form B-II | Form changed (3 days) | Form changed | Form changed |
| Form B-III | Form unchanged (5 days) | Form unchanged | Form unchanged |

Figure 17:
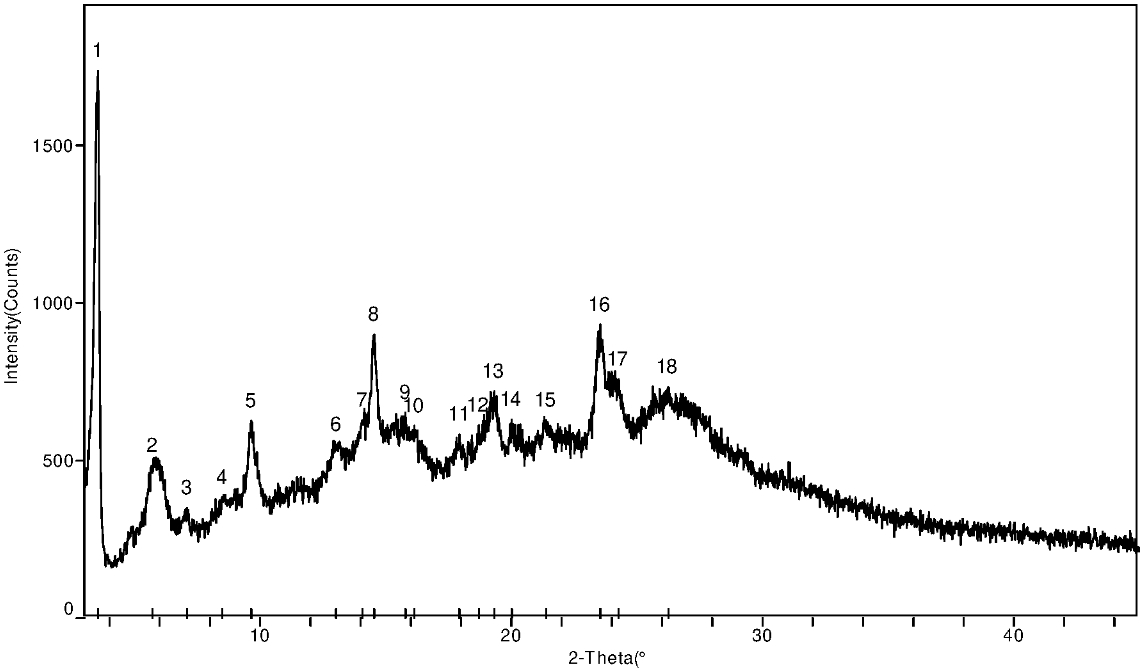
FIG. 17 shows an X-ray powder diffraction pattern of Form B-II of hemitartrate of Compound 78 after being placed under the condition of high humidity (25° C., the relative humidity of 92.5%±5%) for 3 days, wherein the horizontal axis (X-axis) plots the diffraction angle 2 theta, and the vertical axis (Y-axis) plots the diffraction intensity.
Figure 18:
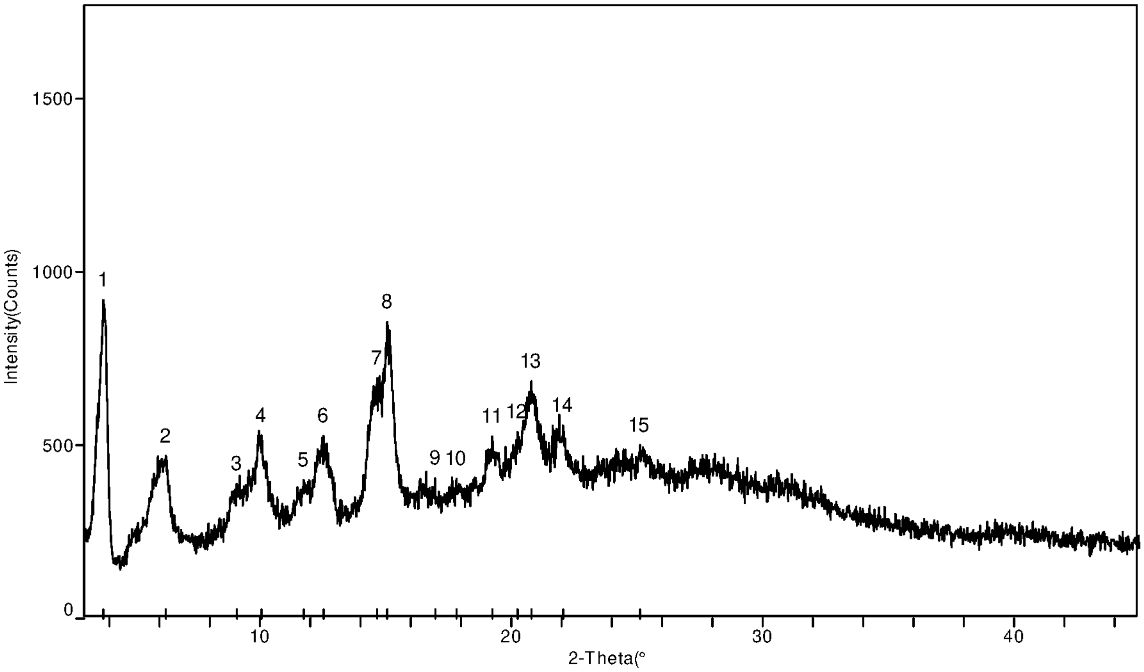
FIG. 18 shows an X-ray powder diffraction pattern of Form B-II of hemitartrate of Compound 78 after being slurried in water for 2 days, wherein the horizontal axis (X-axis) plots the diffraction angle 2 theta, and the vertical axis (Y-axis) plots the diffraction intensity.
Figure 19:
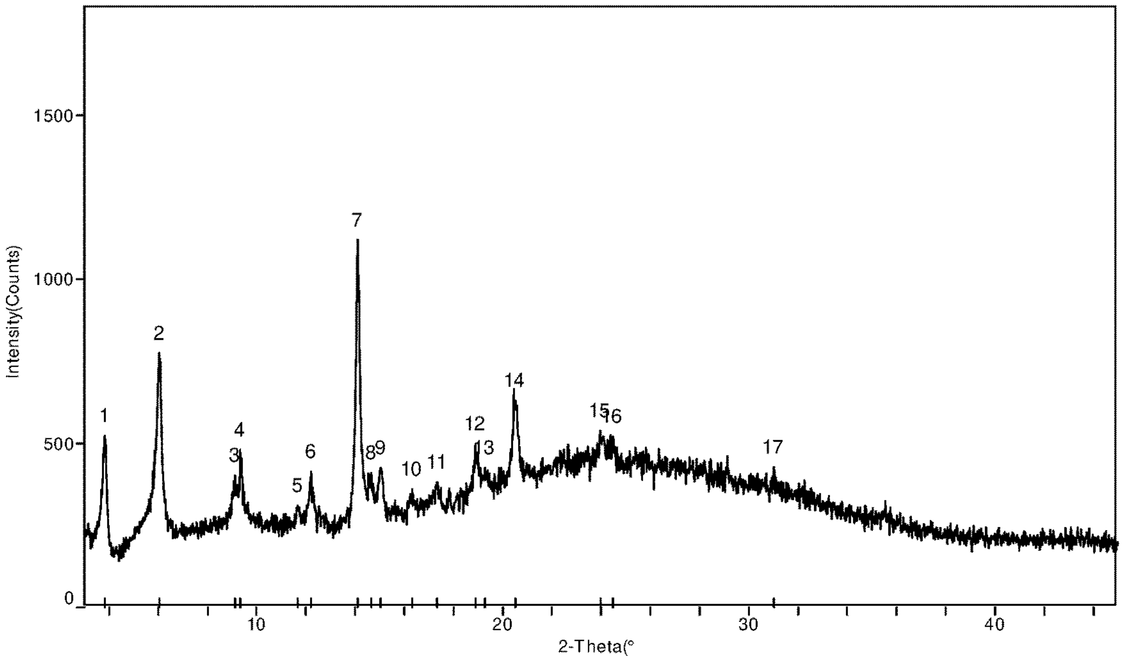
FIG. 19 shows an X-ray powder diffraction pattern of Form B-II of hemitartrate of Compound 78 after being slurried in water for 4 days, wherein the horizontal axis (X-axis) plots the diffraction angle 2 theta, and the vertical axis (Y-axis) plots the diffraction intensity.
Figure 20:
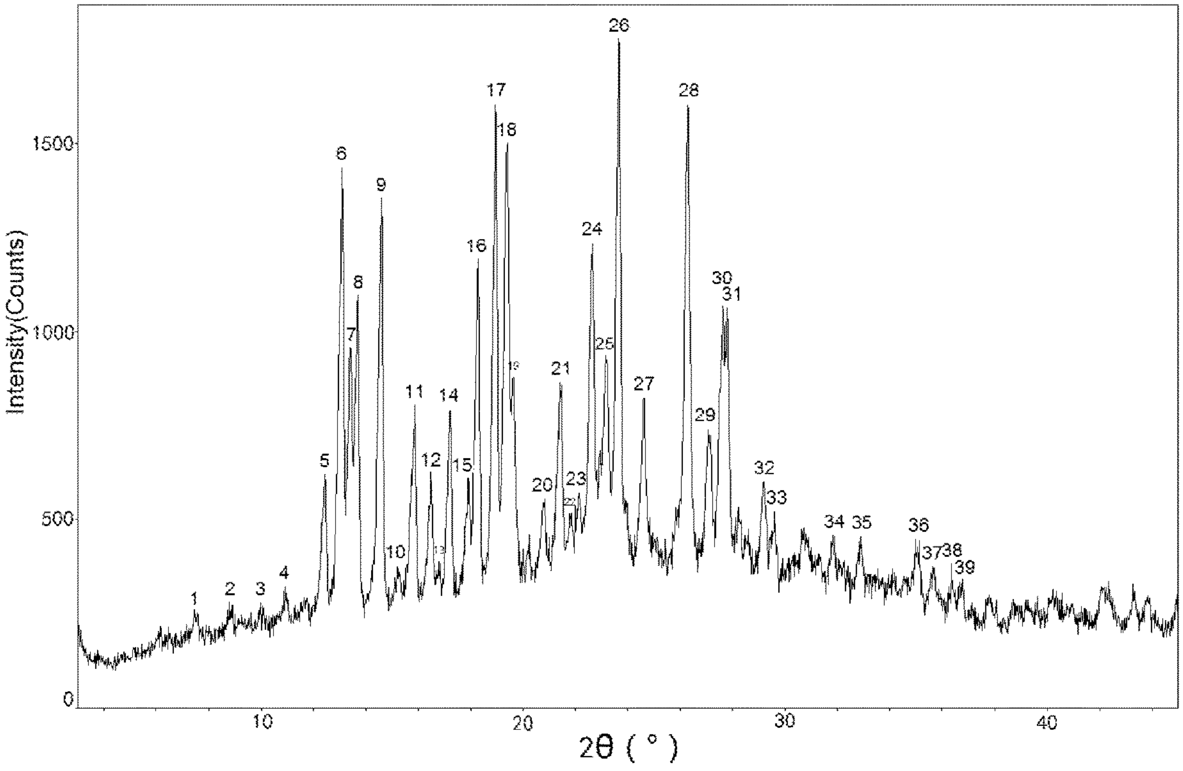
FIG. 20 shows an X-ray powder diffraction pattern of Form B-III of hemitartrate of Compound 78 after being slurried in water for 2 days, wherein the horizontal axis (X-axis) plots the diffraction angle 2 theta, and the vertical axis (Y-axis) plots the diffraction intensity.
Figure 21:
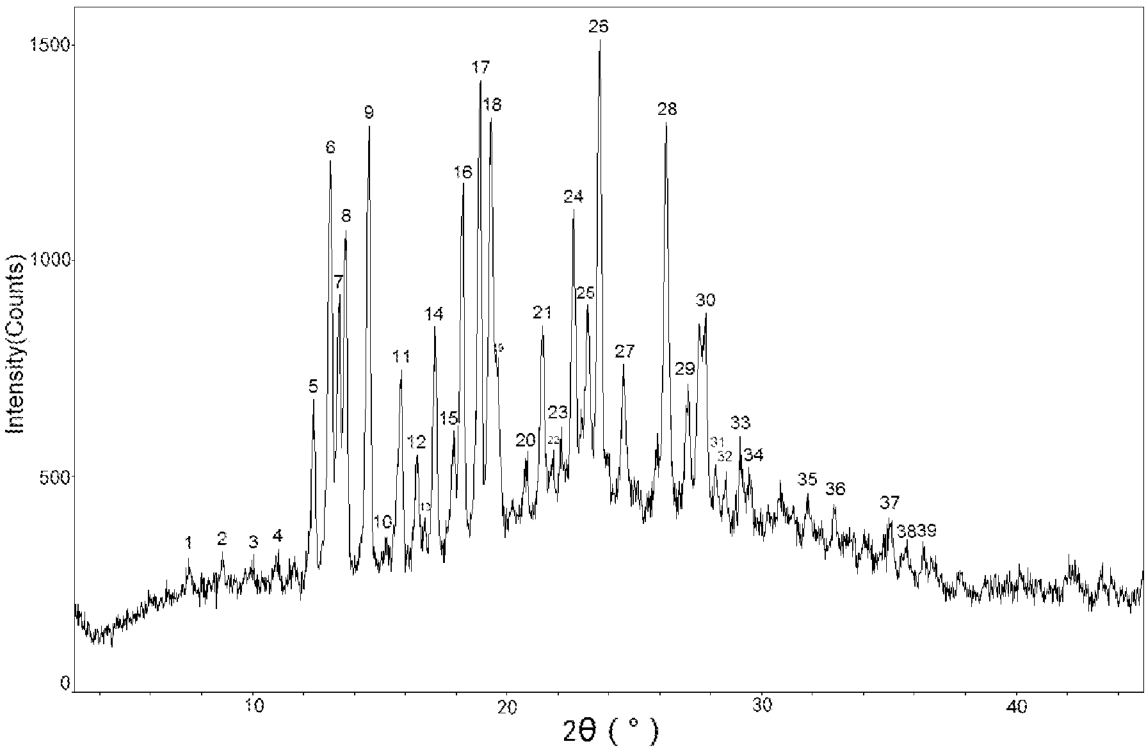
FIG. 21 shows an X-ray powder diffraction pattern of Form B-III of hemitartrate of Compound 78 after being slurried in water for 4 days, wherein the horizontal axis (X-axis) plots the diffraction angle 2 theta, and the vertical axis (Y-axis) plots the diffraction intensity.

The data in Table 2 showed that Form B-II of hemitartrate of Compound 78 was unstable under both test conditions, the presence of moisture water induced the change of the crystalline form (as shown in FIGS. 17-19). By contrast, the crystalline form of Form B-III of hemitartrate of Compound 78 was kept unchanged when being placed under high humidity condition or slurried in water (as shown in FIGS. 20 and 21). Form B-III had a better stability.

Example 19—Solubility Comparison of the Salts of Formula a and the Free Form of Compound 78 in Different Buffers Determination method: excess amount of samples of Form B-III of hemitartrate of Compound 78, Form C-I of mono p-tosylate of Compound 78, and Compound 78 in free form were suspended in the buffers with different pHs and in water respectively, stirred at the constant temperature of 37° C. for 30 minutes, centrifuged, and filtered, and the filtrate was used for determining solubility of the samples. The solubility results were all calculated based on the free form. The results were shown in Table 3. The buffers with different pHs were prepared according to the United States Pharmacopeia (USP40-NF35).

TABLE 3

Solubility of the salts of Formula A and the free form of Compound 78 in different media

| Dissolution Media | Solubility (mg/ml) Form B-III of hemitartrate | Form C-I of mono p-tosylate | Free form |
|---|---|---|---|
| pH 1.2 | 1.6042 | 0.3589 | 0.7207 |
| pH 2.1 | 0.3334 | 0.1023 | 0.1741 |
| pH 4.5 | 0.5415 | 0.0383 | 12.5888 |
| pH 6.8 | 0.0461 | 0.0335 | 0.0675 |
| Purified water | 0.3281 | 0.0287 | 0.0023 |

The data in Table 3 showed that Form B-III of hemitartrate of Compound 78 had very good solubility in the medium of pH 1.2, and also had good solubility in purified water, and showed significantly higher solubility than Form C-I and the free form. Form C-I of mono p-tosylate of Compound 78 had lower but stable solubility in all test media. The free form of Compound 78 had greatly different solubility in different media. More specifically, the free form of Compound 78 had a solubility of up to 12.6 mg/ml in pH 4.5 buffer, but a lower solubility in other media and purified water.

These results showed that the salts of the present invention and the crystalline forms of the present invention had better solubility profile. In one aspect, as compared to Compound 78 in free form, the salts of the present invention had smaller solubility difference at different pH values, rendering the solubility of the salts of the present invention in the body fluid with different pH values more stable. In another aspect, the salts of the present invention and the crystalline forms of the present invention still had high and stable solubility at the high pH condition of gastrointestinal tract, which is beneficial to its sufficient absorption, thereby resulting in higher bioavailability and avoiding the influence of foods on the drug absorption in vivo.

Example 20—Hygroscopicity of the Salts of Formula a

Determination method: the test samples of Form B-III and Form B-II of hemitartrate of Compound 78 were placed in the sample dishes of the Dynamic Vapor Sorption instrument (DVS-INTRINSIC) respectively. Then the weight gains by moisture absorption of the samples were measured at a relative humidity of 0-95% at 25° C. The results were shown in FIGS. 10 and 11.

Figure 10:
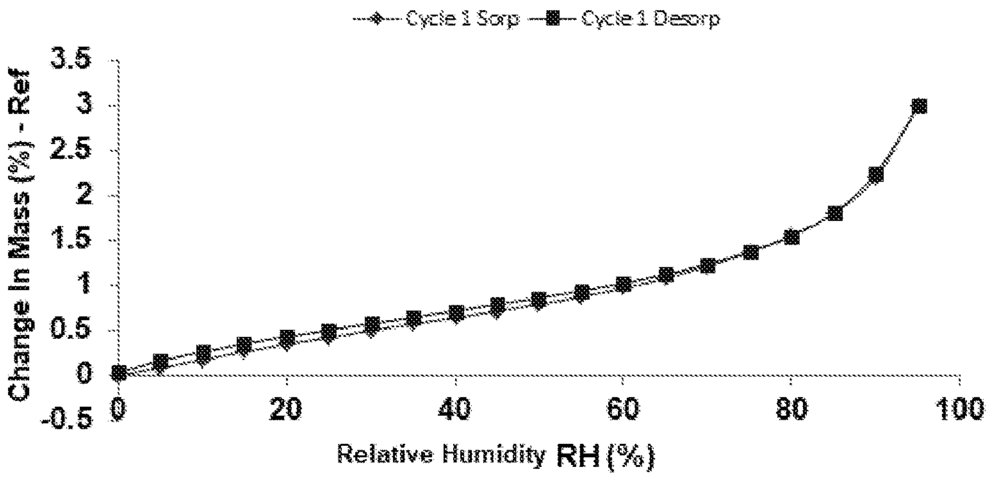
FIG. 10 shows a dynamic vapor sorption (DVS) isotherm plot of Form B-III of hemitartrate of Compound 78, wherein the horizontal axis (X-axis) plots the relative humidity (%), and the vertical axis (Y-axis) plots the weight change percentage (%).

The curve of FIG. 10 showed that Form B-III of hemitartrate of Compound 78 was not hygroscopic when the ambient humidity was lower than 85% RH, and was slightly hygroscopic when the ambient humidity was higher than 85% RH.

Figure 11:
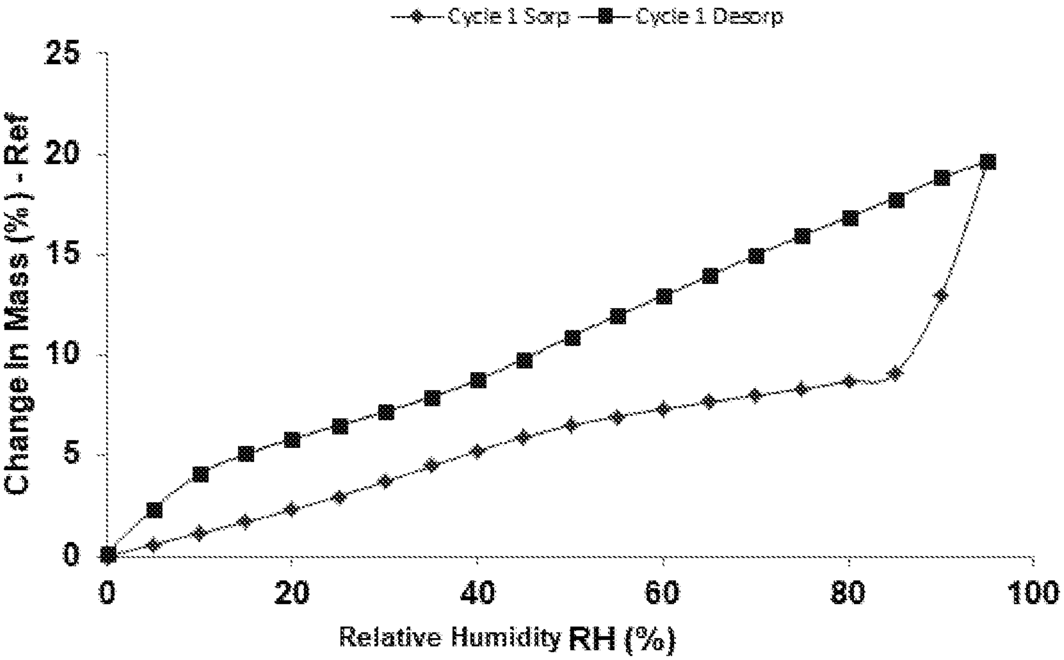
FIG. 11 shows a dynamic vapor sorption (DVS) isotherm plot of Form B-II of hemitartrate of Compound 78, wherein the horizontal axis (X-axis) plots the relative humidity (%), and the vertical axis (Y-axis) plots the weight change percentage (%).

The curve of FIG. 11 showed that Form B-II of hemitartrate of Compound 78 was continuously hygroscopic at 0 to 80% RH, and its hygroscopicity was further increased when the ambient humidity was higher than 85% RH. After the sample absorbed moisture, the absorbed moisture caused hysteresis in the desorption process.

Example 21—Pharmacokinetic Study of the Salts of Formula a in Dogs

Preparation of Formulations

IV formulation: 71.48 mg of Form B-III of hemitartrate of Compound 78 was dissolved in a mixture of 10% Macrogol-15 hydroxyl stearate (Solutol), 10% ethanol and 80% saline (60.7 ml), to give a clear solution for IV administration.

PO formulation (0.5 mg/ml on the basis of the concentration of the free form): 71.54 mg of Form B-III of hemitartrate of Compound 78 was suspended in 121.5 ml of deionized water, to give a suspension for PO administration to dogs in the 1 mg/kg dosing groups.

Dosing and Sampling

The experimental design was shown in Table 4 below:

| Period | Group | Compound and formulation | Number of animals (N) | Dosing route | Dosing amount mg/kg | Dosing Volume ml/kg |
|---|---|---|---|---|---|---|
| 1 | 1 | Form B-III of hemitartrate of Compound 78 formulated in a mixture of 10% Solutol, 10% ethonal and 80% saline | 3 male/3 female | IV bolus | 1 | 1 |
| | 2 | Form B-III of hemitartrate of Compound 78 formulated in purified water | 3 male/3 female | PO | 1 | 2 |

The sampling time points were shown in Table 5 below:

| Period | Group | Dosing amount (mg/kg) IV | PO | Days | Sampling time points |
|---|---|---|---|---|---|
| 1 | 1 | 1 | — | Day 1 and day 2 | 0, 2, 5, 15, 30 minutes, and 1, 2, 3, 4, 6, 8, 10, 12, 24 hours |
| | 2 | — | 1 | Day 1 and day 2 | 0, 15, 30 minutes, and 1, 1.5, 2, 3, 4, 5, 6, 8, 10, 12, 24 hours |

Biological Sample Analysis Method

A LC-MS/MS method was used for the determination of the concentration of the free form of Compound 78 in dog plasma.

Data Analysis

The data was analyzed using non-compartmental statistical moment method and pharmacokinetic software Phoenix (version, 6.2.1.51) to calculate PK parameters of each group. The $C_{max}$ and $T_{max}$ were given as measured values. The absolute bioavailability (F %) was calculated by the following Equation:

$$(AUC_{0-\infty,PO} \times Dosage_{IV})/(AUC_{0-\infty,IV} \times Dosage_{PO})$$

Wherein $AUC_{0-\infty,PO}$ is the exposure of the free form of Compound 78 after oral administration in dogs ($AUC_{0-\infty}$); $AUC_{0-\infty,IV}$ is the exposure of the free form of Compound 78 after IV administration in dogs ($AUC_{0-\infty}$); $Dosage_{IV}$ is the dosing amount of IV administration; $Dosage_{PO}$ is the dosing amount of oral administration.

Results and Discussion

The average values of main pharmacokinetic parameters of Form B-III of hemitartrate of Compound 78 in dogs were shown in Table 6 and Table 7.

After intravenous administration of Form B-III of hemitartrate of Compound 78 (the content of Compound 78 in free form was 1.0 mg/kg), the overall average exposure in dogs ($AUC_{0-\infty}$) was 1880±349 h-ng/ml; the overall average clearance (CL) was 9.09±1.51 ml/min/kg; the overall average plasma elimination half-life ($t_{1/2}$) was 5.90±0.645 h; the overall average steady-state distribution volume ($V_{ss}$) was 2.95±0.399 L/kg.

After oral administration of Form B-III of hemitartrate of Compound 78 (the content of Compound 78 in free form was 1.0 mg/kg, fasted state), the overall average time to peak of plasma concentration in dogs ($T_{max}$) was 0.792±0.459 h; the overall maximum average concentration ($C_{max}$) was 141±68.8 ng/ml; the overall average exposure ($AUC_{0-\infty}$) was 665±276 h·ng/ml; the overall average plasma elimination half-life ($t_{1/2}$) was 5.36±1.69 h; the overall average absolute bioavailability (F %) was 35.4%.

TABLE 6

The average values of pharmacokinetic parameters after IV injection of Form B-III of hemitartrate of Compound 78 at 1.0 mg/kg in dogs

| Period | Dosing route | Dosing amount (mg/kg) | | $t_{1/2}$ (h) | $C_0$ (ng/ml) | CL (ml/min/kg) | $V_{ss}$ (L/kg) | MRT (h) | $AUC_{last}$ (h · ng/ml) | $AUC_{0-\infty}$ (h · ng/ml) |
|---|---|---|---|---|---|---|---|---|---|---|
| 1 | IV injection | 1.00 | Average in male | 5.69 | 2630 | 9.25 | 2.88 | 5.33 | 1830 | 1890 |
| | | | SD | 0.762 | 811 | 2.30 | 0.419 | 0.990 | 499 | 539 |
| | | | N | 3 | 3 | 3 | 3 | 3 | 3 | 3 |
| | | | Average in female | 6.11 | 2720 | 8.92 | 3.02 | 5.64 | 1810 | 1870 |
| | | | SD | 0.574 | 459 | 0.551 | 0.455 | 0.729 | 126 | 118 |
| | | | N | 3 | 3 | 3 | 3 | 3 | 3 | 3 |
| | | | Overall average | 5.90 | 2670 | 9.09 | 2.95 | 5.48 | 1820 | 1880 |
| | | | SD | 0.645 | 591 | 1.51 | 0.399 | 0.796 | 326 | 349 |
| | | | N | 6 | 6 | 6 | 6 | 6 | 6 | 6 |

TABLE 7

The average values of pharmacokinetic parameters after administration by gavage of Form B-III of hemitartrate of Compound 78 at 1.0 mg/kg in dogs

| Period | Dosing route | Dosing amount (mg/kg) | | $t_{1/2}$ (h) | $T_{max}$ (h) | $C_{max}$ (ng/ml) | MRT (h) | $AUC_{last}$ (h · ng/ml) | $AUC_{0-\infty}$ (h · ng/ml) | F % |
|---|---|---|---|---|---|---|---|---|---|---|
| 1 | gavage | 1.00 | Average in male | 4.47 | 1.00 | 137 | 5.48 | 663 | 687 | 36.3 |
| | | | SD | 1.87 | 0.500 | 55.3 | 1.27 | 232 | 235 | |
| | | | N | 3 | 3 | 3 | 3 | 3 | 3 | |
| | | | Average in female | 6.24 | 0.583 | 144 | 6.09 | 621 | 643 | 34.4 |
| | | | SD | 1.13 | 0.382 | 93.5 | 0.800 | 362 | 365 | |
| | | | N | 3 | 3 | 3 | 3 | 3 | 3 | |
| | | | Overall average | 5.36 | 0.792 | 141 | 5.79 | 642 | 665 | 35.4 |
| | | | SD | 1.69 | 0.459 | 68.8 | 1.01 | 273 | 276 | |
| | | | N | 6 | 6 | 6 | 6 | 6 | 6 | |

CONCLUSION

After administration by gavage of Form B-III of hemitartrate of Compound 78 at a single dose of 1 mg/kg in beagle dogs, a good oral absorption in vivo was shown in dogs with the absolute oral bioavailability of about 35.4%. Form B-III of hemitartrate of Compound 78 had a quick absorption in dogs with $T_{max}$ of about 1 hour. After administration by intravenous injection of Form B-III of hemitartrate of Compound 78 at a single dose of 1 mg/kg, the clearance (CL) in dogs was 9.09±1.51 ml/min/kg, indicating that it was a low clearance drug. The $V_{ss}$ was 2.95±0.40 L/kg, indicating a wide distribution. In summary, Form B-III of hemitartrate of Compound 78 showed good pharmacokinetic characteristics in dogs.

It is to be understood that, the examples and embodiments described herein are only for illustration, and various practicable improvements or modifications of the embodiments of the present invention would be suggested to those skilled in the art by the disclosure and are within the spirit and scope of the present application and the scope of the appended claims. All the publications, patents and patent applications cited herein are incorporated herein by reference for all purposes.

What is claimed:

1. A salt of Formula A:

Formula A

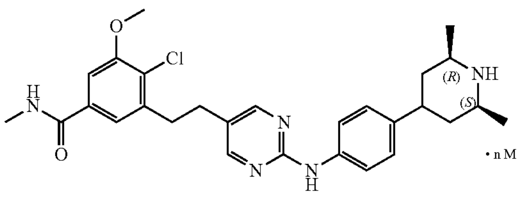

wherein (i) n is 1 and M is hydrochloric acid, and the salt is Form A-III having the X-ray powder diffraction characteristic diffraction angles (2θ) of 5.8±0.2°, 6.2±0.2°, 12.3±0.2°, 13.3±0.2°, 23.1±0.2°, and 24.1±0.2°;

(ii) n is 0.5 and M is tartaric acid, and the salt is Form B-II having the X-ray powder diffraction characteristic diffraction angles (2θ) of 7.5±0.2°, 11.3±0.2°, 13.9±0.2°, 15.1±0.2°, 18.0±0.2°, and 20.6±0.2°;

(iii) n is 0.5 and M is tartaric acid, and the salt is Form B-III having the X-ray powder diffraction characteristic diffraction angles (2θ) of 13.1±0.2°, 14.6±0.2°, 18.3±0.2°, 18.9±0.2°, 19.4±0.2°, and 26.3±0.2°; or (iv) n is 1 and M is p-toluenesulfonic acid, and the salt is Form C-I having the X-ray powder diffraction characteristic diffraction angles (2θ) of 7.8±0.2°, 11.1±0.2°, 11.7±0.2°, 16.6±0.2°, 17.9±0.2°, 18.2±0.2°, 19.2±0.2°, and 24.0±0.2°.

2. The salt of Formula A according to claim 1, wherein the salt is Form A-III and said Form A-III has the X-ray powder diffraction characteristic diffraction angles (2θ) of 5.8±0.2°, 6.2±0.2°, 10.3±0.2°, 12.3±0.2°, 13.3±0.2°, 15.0±0.2°, 16.2±0.2°, 22.2±0.2°, 23.1±0.2°, 24.1±0.2°, and 26.4±0.2°.

3. The salt of Formula A according to claim 1, wherein the salt is Form B-II and said Form B-II has the X-ray powder diffraction characteristic diffraction angles (2θ) of 3.8±0.2°, 7.5±0.2°, 11.3±0.2°, 13.9±0.2°, 15.1±0.2°, 15.7±0.2°, 18.0±0.2°, 19.8±0.2°, 20.6±0.2°, 21.7±0.2°, and 23.0±0.2°.

4. The salt of Formula A according to claim 1, wherein the salt is Form B-III and said Form B-III has the X-ray powder diffraction characteristic diffraction angles (2θ) of 12.4±0.2°, 13.1±0.2°, 13.7±0.2°, 14.6±0.2°, 16.5±0.2°, 18.3±0.2°, 18.9±0.2°, 19.4±0.2°, 21.4±0.2°, 22.6±0.2°, 23.7±0.2°, and 26.3±0.2°.

5. The salt of Formula A according to claim 1, wherein the salt is Form B-III and said Form B-III has the differential scanning calorimetry (DSC) curve having an endothermic peak at about 269.2-271.3° C.

6. The salt of Formula A according to claim 1, wherein the salt is Form B-III and said Form B-III has a thermogravimetric analysis (TGA) curve as shown in FIG. 9.

7. The salt of Formula A according to claim 1, wherein the salt is Form C-I and said Form C-I has the X-ray powder diffraction characteristic diffraction angles (2θ) of 5.5±0.2°, 7.8±0.2°, 9.7±0.2°, 11.1±0.2°, 11.7±0.2°, 13.8±0.2°, 14.3±0.2°, 16.6±0.2°, 17.9±0.2°, 18.2±0.2°, 19.2±0.2°, 22.2±0.2°, 24.0±0.2°, and 26.1±0.2°.

8. The salt of Formula A according to claim 1 for use in the treatment of a disease responsive to inhibition of FGFR activity, which is a cancer selected from lung cancer, gastric cancer, liver cancer, breast cancer, ovarian cancer, endometrial cancer, bladder cancer, urothelial cancer, esophageal cancer, biliary tract cancer, colon cancer, rectal cancer, head and neck cancer, cervical cancer, pancreatic cancer, adrenal cancer, glioma, mesothelioma, and hematologic malignancy.

9. A method for preparing the salt of Formula A according to claim 1, wherein the salt is Form A-III, and the method comprises:

(1) mixing the compound 4-chloro-3-(2-(2-((4-((3S,5R)-3,5-dimethylpiperazin-1-yl) phenyl)amino)pyrimidin-5-yl)ethyl)-5-methoxy-N-methylbenzamide with hydrochloric acid in a dissolution solvent or in a mixed solvent consisting of water miscible organic solvent and water under heating and stirring for reacting to form a salt;

(2) cooling the reaction obtained in step (1) to precipitate the solid;

(3) isolating the precipitated solid as Form A-III;

(4) optionally drying the solid obtained in step (3), wherein said hydrochloric acid is concentrated hydrochloric acid with the concentration of 36%-38% by weight, the molar ratio of said hydrochloric acid to said compound 4-chloro-3-(2-(2-((4-((3S,5R)-3,5-dimethylpiperazin-1-yl) phenyl)amino)pyrimidin-5-yl)ethyl)-5-methoxy-N-methylbenzamide is not less than about 1:1, the ratio of the volume of said dissolution solvent or said mixed solvent to the weight of said compound 4-chloro-3-(2-(2-((4-((3S,5R)-3,5-dimethylpiperazin-1-yl)phenyl)amino)pyrimidin-5-yl) ethyl)-5-methoxy-N-methylbenzamide is not less than about 10 ml/g, said dissolution solvent is selected from $C_{1-6}$ alkanol, said water miscible organic solvent is selected from $C_{1-6}$ alkanol, the volume percentage of said water miscible organic solvent in said mixed solvent is not more than about 95%, and in the optional step (4), the drying temperature is 50-80° C.

10. A method for preparing the salt of Formula A according to claim 1, wherein the salt is Form B-II, and the method comprises:

(1) mixing the compound 4-chloro-3-(2-(2-((4-((3S,5R)-3,5-dimethylpiperazin-1-yl)phenyl) amino)pyrimidin-5-yl)ethyl)-5-methoxy-N-methylbenzamide with L-tartaric acid in ethanol under heating and stirring for reacting to form a salt;

(2) cooling the reaction obtained in step (1) to precipitate the solid;

(3) isolating the precipitated solid as Form B-II;

(4) optionally drying the solid obtained in step (3), wherein the molar ratio of said L-tartaric acid to said compound 4-chloro-3-(2-(2-((4-((3S,5R)-3,5-dimethylpiperazin-1-yl)phenyl)amino)pyrimidin-5-yl) ethyl)-5-methoxy-N-methylbenzamide is not less than about 1:2, the ratio of the volume of said ethanol to the weight of said compound 4-chloro-3-(2-(2-((4-((3S,5R)-3,5-dimethylpiperazin-1-yl)phenyl)amino)pyrimidin-5-yl) ethyl)-5-methoxy-N-methylbenzamide is not less than about 10 ml/g, and in the optional step (4), the drying temperature is 50-85° C.

11. A method for preparing the salt of Formula A according to claim 1, wherein the salt is Form B-III, and the method comprises:

(1) mixing the compound 4-chloro-3-(2-(2-((4-((3S,5R)-3,5-dimethylpiperazin-1-yl)phenyl) amino)pyrimidin-5-yl)ethyl)-5-methoxy-N-methylbenzamide with L-tartaric acid in a dissolution solvent, in water, or in a mixed solvent consisting of water miscible organic solvent and water under heating and stirring for reacting to form a salt, thereby obtaining the first solution; provided that said dissolution solvent is not the single solvent ethanol;

(2) optionally adding an anti-dissolution solvent into said first solution to obtain the second solution;

(3) cooling said first solution or second solution to precipitate the solid;

(4) isolating the precipitated solid as Form B-III;

(5) optionally drying the solid obtained in step (4), wherein said dissolution solvent is selected from $C_{1-6}$ alkanol, acetone, toluene, organic acid ester with not more than eight carbon atoms, and the mixture thereof, said dissolution solvent is selected from a mixed solvent consisting of two solvents of methanol, ethanol, toluene, n-propyl acetate, and ethyl acetate, for example, n-propyl acetate/methanol (in the volume ratio of about 3:2), toluene/ethanol (in the volume ratio of about 1:1), or ethyl acetate/ethanol (in the volume ratio of about 11:15), said water miscible organic solvent is selected from $C_{1-6}$ alkanol, acetone, and the mixture thereof, the volume percentage of said water miscible organic solvent in said mixed solvent is not more than about 95%, and said anti-dissolution solvent is selected from toluene, organic acid ester with not more than eight carbon atoms, and the mixture thereof.

12. A method for preparing the salt of Formula A according to claim 1, wherein the salt is Form C-I, and the method comprises:

(1) mixing the compound 4-chloro-3-(2-(2-((4-((3S,5R)-3,5-dimethylpiperazin-1-yl) phenyl)amino)pyrimidin-5-yl)ethyl)-5-methoxy-N-methylbenzamide with p-toluenesulfonic acid monohydrate in a mixed solvent consisting of water miscible organic solvent and water under heating and stirring for reacting to form a salt;

(2) cooling the reaction obtained in step (1) to precipitate the solid;

(3) isolating the precipitated solid as Form C-I;

(4) optionally drying the solid obtained in step (3), wherein the molar ratio of said p-toluenesulfonic acid monohydrate to said compound 4-chloro-3-(2-(2-((4-((3S,5R)-3,5-dimethylpiperazin-1-yl)phenyl) amino)pyrimidin-5-yl)ethyl)-5-methoxy-N-methylbenzamide is not less than about 1:1, the ratio of the volume of said mixed solvent consisting of water miscible organic solvent and water to the weight of said compound 4-chloro-3-(2-(2-((4-((3S,5R)-3,5-dimethylpiperazin-1-yl)phenyl)amino)pyrimidin-5-yl) ethyl)-5-methoxy-N-methylbenzamide in step (1) is not less than about 10 ml/g, said water miscible organic solvent is selected from $C_{1-6}$ alkanol, acetone, and the mixture thereof, the volume percentage of said water miscible organic solvent in said mixed solvent is not more than about 95%, after the completion of the reaction in step (1), an anti-dissolution solvent is optionally added prior to step (2), in step (2), said cooling is cooling naturally or cooling at a controlled temperature, and in the optional step (4), the drying temperature is 50-60° C.

13. The method according to claim 11, wherein the molar ratio of said L-tartaric acid to said compound 4-chloro-3-(2-(2-((4-((3S,5R)-3,5-dimethylpiperazin- 1-yl)phenyl)amino)pyrimidin-5-yl) ethyl)-5-methoxy-N-methylbenzamide is not less than about 1:1, the ratio of the volume of said dissolution solvent, said water, or said mixed solvent consisting of water miscible organic solvent and water to the weight of said compound 4-chloro-3-(2-(2-((4-((3S,5R)-3,5-dimethylpiperazin-1-yl)phenyl)amino)pyrimidin-5-yl)ethyl)-5-methoxy-N-methylbenzamide is not less than about 10 ml/g, in step (3), said cooling is cooling naturally or cooling at a controlled temperature, and in step (5), the drying temperature is 50-85° C.

14. A pharmaceutical composition, comprising an effective amount of the salt of Formula A according to claim 3, and optionally a pharmaceutically acceptable carrier.

15. A method of preventing or treating a disease responsive to inhibition of FGFR activity, which is cancer, comprising administering to a subject in need thereof an effective amount of the salt of Formula A according to claim 3.

16. The method according to claim 15, wherein said cancer is selected from lung cancer, gastric cancer, liver cancer, breast cancer, ovarian cancer, endometrial cancer, bladder cancer, urothelial cancer, esophageal cancer, biliary tract cancer, colon cancer, rectal cancer, head and neck cancer, cervical cancer, pancreatic cancer, adrenal cancer, glioma, mesothelioma, and hematologic malignancy.

* * * * *